US008334259B2

(12) United States Patent
Carney et al.

(10) Patent No.: US 8,334,259 B2
(45) Date of Patent: Dec. 18, 2012

(54) METHOD OF TREATING ENDOTHELIAL DYSFUNCTION COMPRISING ADMINISTRATION OF A THROMBIN PEPTIDE DERIVATIVE

(75) Inventors: Darrell H. Carney, Dickinson, TX (US); Barbara Olszewska-Pazdrak, League City, TX (US); Theresa W. Fossum, College Station, TX (US)

(73) Assignees: The Board of Regents, The University of Texas System, Austin, TX (US); The Texas A&M University System, College Station, TX (US)

( * ) Notice: Subject to any disclaimer, the term of this patent is extended or adjusted under 35 U.S.C. 154(b) by 625 days.

(21) Appl. No.: 12/311,130

(22) PCT Filed: Sep. 21, 2007

(86) PCT No.: PCT/US2007/020445
§ 371 (c)(1),
(2), (4) Date: Jun. 3, 2009

(87) PCT Pub. No.: WO2008/036387
PCT Pub. Date: Mar. 27, 2008

(65) Prior Publication Data
US 2009/0304671 A1    Dec. 10, 2009

Related U.S. Application Data

(60) Provisional application No. 60/922,646, filed on Apr. 10, 2007, provisional application No. 60/848,004, filed on Sep. 28, 2006, provisional application No. 60/846,418, filed on Sep. 22, 2006.

(51) Int. Cl.
*A61P 9/12* (2006.01)
*A61P 39/06* (2006.01)

(52) U.S. Cl. ............... 514/15.7; 514/15.1; 514/21.4; 514/21.5; 514/917; 530/326; 530/327

(58) Field of Classification Search ............... None
See application file for complete search history.

(56) References Cited

U.S. PATENT DOCUMENTS

| | | |
|---|---|---|
| 5,244,460 A | 9/1993 | Unger |
| 5,352,664 A | 10/1994 | Carney et al. |
| 5,500,412 A | 3/1996 | Carney et al. |
| 5,912,229 A | 6/1999 | Thim |
| 6,033,436 A | 3/2000 | Steinke |
| 6,191,113 B1 | 2/2001 | Nakahara |
| 6,197,751 B1 | 3/2001 | Malinda |
| 6,363,938 B2 | 4/2002 | Saadat |
| 6,627,731 B1 | 9/2003 | Carney et al. |
| 6,861,407 B2 | 3/2005 | Carney |
| 6,867,190 B2 | 3/2005 | Carney |
| 7,034,001 B2 * | 4/2006 | Carney .................. 514/9.4 |
| 7,214,661 B2 | 5/2007 | Carney |
| 7,456,250 B2 | 11/2008 | Carney |
| 7,732,411 B2 | 6/2010 | Carney |
| 2002/0061852 A1 | 5/2002 | Carney |
| 2002/0187933 A1 | 12/2002 | Carney |
| 2005/0153884 A1 * | 7/2005 | Carney .................. 514/12 |
| 2005/0153893 A1 * | 7/2005 | Carney .................. 514/12 |

FOREIGN PATENT DOCUMENTS

| | | |
|---|---|---|
| WO | WO 88/03151 | 5/1988 |
| WO | WO 94/25056 | 11/1994 |
| WO | WO 99/53943 | 10/1999 |
| WO | WO 00/24412 | 5/2000 |
| WO | WO 02/04008 | 1/2002 |
| WO | WO 03/061689 | 7/2003 |
| WO | WO 2004/014937 | 2/2004 |

OTHER PUBLICATIONS

Fossum et al (2008. Journal of Cardiovascular Pharmacology and Therapeutics. 13(3): 214-225).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Phillips, J Pharm Pharmacology 53: 1169-1174, 2001.*
Soloviev et al, 2003. British Journal of Pharmacology. 138: 837-844.*
Hatoum et al, 2006. Arterioscler Thromb Vasc Biol. 26: 287-294.*
International Search Report and Written Opinion—(PCT/US2007/020445) Date of Mailing Oct. 10, 2008.
Bosnjak, et al., "Mechanism of Thrombin-Induced Vasodilation in Human Coronary Arterioles", American Journal of Physiology—Heart and Circulatory Physiology, 2003, vol. 284, pp. H1080-H1086.
Davignon, et al., "Role of Endothelial Dysfuction in Atherosclerosis", Circulation, 2004, vol. 109, pp. III27-III32, Abstract, XP002493378.
Hamilton, et al., "Atypical Protease-activated Receptor Mediates Endothelium-Dependent Relaxation of Human Coronary Arteries", Circulation Research, 1998, vol. 82, pp. 1306-1311.
Mizuno, et al., "Mechanism of Endothelium-dependent Relaxation Induced by Thrombin in the Pig Coronary Artery", European Journal of Pharmacology, 1998, vol. 351, pp. 67-77.
Olszewska-Pazdrak, et al., "TP508 Peptide Restores VEGF-induced Activation of eNOS in Hypoxic Human Endothelial Cells", Arteriosclerosis, Thrombosis, and Vascular Biology, 2007, vol. 27, pp. E-75, Abstract, XP002491348.
Olszewska-Pazdrak, et al., "Effect of Thrombin Peptide TP508 on Cultured Endothelial Cells Suggest a Wound Healing Mode of Action that Involves Reversal of Endothelial Dysfunction", Wound Repair Regeneration, 2007, vol. 15, p. A32, Abstract, XP002491320.

(Continued)

Primary Examiner — Zachary Howard
(74) Attorney, Agent, or Firm — Mueting, Raasch & Gebhardt, P.A.

(57) ABSTRACT

Endothelial dysfunction (ED) is associated with a number of diseases and disorders. Agonists of the non-proteolytically activated thrombin receptor can be used in methods to treat ED or ED-related diseases and disorders.

28 Claims, 13 Drawing Sheets

OTHER PUBLICATIONS

Tesfamariam, et al., "Involvement of the 'tethered ligand' receptor in thrombin-induced endothelium-mediated relaxations", 1993, Abstract, XP002493379, Database Biosis, Biosciences Information Service, Philadelphia, PA US ).

Aoki, M., et al., "Angiogenesis induced by hepatocyte growth factor in non-infarcted myocardium and infarcted myocardium: up-regulation of essential transcription factor for angiogenesis" Gene Therapy, 7(5):417-427, (2000).

Carney, D.H., "Postclotting Cellular Effects of Thrombin Mediated by Interaction with High-Affinity Thrombin Receptors," Thrombin: Structure and Function, Chapter 10, pp. 351-396, (1992).

Carney, D.H., et al., "Enhancement of Incisional Wound Healing and Neovascularization in Normal Rats by Thrombin and Synthetic Thrombin Receptor-activating Peptides," J. Clin. Invest., 89:1469-1477, (1992).

Chen, S.J., et al., "Mithramycin Inhibits Myointimal Proliferation After Balloon Injury of the Rat Carotid Artery in Vivo," Circulation, 90(5):2468-2473, (1994).

Coleman, C.L., et al., "Systemic Injection of Thrombin Peptide TP508 Mitigates Angioplasty-related Restenosis in Hypercholesterolemic Rabbit Iliac Arteries," Abstract LB14, Presented at the Experimental Biology 2001 Meeting (Orlando, Florida).

Folkman, J., "Angiogenic Therapy of the Human Heart," Journal of the American Heart Association, 97(7):628-629, (1998).

Fossum et al., "Healing the Heart: New Options for Repair of Ischemic and Infarcted Myocardium." T. Klin. Karrdiyoloji. 16(s) (2003).

Frimerman, A., et al., "Chimeric DNA-RNA Hammerhead Ribozyme to Proliferating Cell Nuclear Antigen Reduces Stent-Induced Stenosis in a Porcine Coronary Model," Journal of the American Heart Association, 99(5):697-703, (1999).

Glenn, K.C., et al., "Synthetic Peptides Bind to High-Affinity Thrombin Receptors and Modulate Thrombin Mitogenesis," Peptide Research, 1(2):65-73, (1988).

Hendel, R.C., et al., "Effect of Intracoronary Recombinant Human Vascular Endothelial Growth Factor on Myocardial Perfusion," Journal of the American Heart Association, 101(2):118-121, (2000).

Kawasuji, M., et al., "Therapeutic Angiogenesis With Intramyocardial Administration of Basic Fibroblast Growth Factor," The Annals of Thoracic Surgery, 69(4):1155-1161, (2000).

Laham, R.J., et al., "Intracoronary and Intravenous Administration of Basic Fibroblast Growth Factor: Myocardial and Tissue Distribution," Drug Metabolism and Disposition, 27(7):821-826, (1999).

Malinda, Katherine M., et al. "Thymosin Stimulates Endothelial Cell Migration, Angiogenesis, and Wound Healing," The Journal of Immunology, 160: 1001-1006, (1998).

McKenna, C.J. et al., "Selective ET Receptor Antagonism Reduces Neointimal Hyperplasia in a Porcine Coronary Stent Model," Journal of the American Heart Association, 97(25):2551-2556, (1998).

Munro, E., et al., "Inhibition of human vascular smooth muscle cell proliferation by lovastatin: the role of isoprenoid intermediates of cholesterol synthesis," European Journal of Clinical Investigation, 24(11):766-772, (1994).

Nadir, M., et al., "Inhibition of coronary restenosis by antithrombin III in atherosclerotic swine," Coronary Artery Disease, 7(11):851-861, (1996).

Naldini et al., "Thromobin regulates the Expression of Prpangiogenic Cytokines via Proteolytic Activation of Protease-Activated Receptor-1" Gen Pharmacology 35:255-259 (2002).

Norfleet, A.M., et al., "Thrombin Peptide, TP508, Stimulates Angiogenic Responses in Animal Models of Dermal Wound Healing, in Click Chorioallantoic Membranes, and in Cultured Human Aortic and Microvascular Endothelial Cells," Gen. Pharmacology 35:249-254 (2001).

PCT/US02/01396, International Search Report. Board of Regents, the University of Texas System. Sep. 30, 2002.

Pecher, P., and Schumacher, B.A., "Angiogenesis is Ischemic Human Myocardium: Clinical Results After 3 Years," The Annals of Thoracic Surgery, 69(5):1414-1419, (2000).

Rosengart, T.K., et al., "Six-Month Assessment of a Phase I Trial of Angiogenic Gene Therapy for the Treatment of Coronary Artery Disease Using Direct Intramyocardial Administration of an Adenovirus Vector Expressing the VEGF121 cDNA" Annals of Surgery, 230(4):466-472, (1999).

Sellke, F.W., et al., "Therapeutic Angiogenesis With Basic Fibroblast Growth Factor: Technique and Early Results," The Annals of Thoracic Surgery, 65(6):1540-1544, (1998).

Shi, Y., et al., "Downregulation of c-myc Expression by Antisense Oligonucleotides Inhibits Proliferation of Human Smooth Muscle Cells," Circulation, 88(3):1190-1195, (1993).

Sower, L.E., et al., "Thrombin Peptide, TP508, Induces Differential Gene Expression in Fibroblasts through a Nonproteolytic Activation Pathway," Experimental Cell Research, 247:422-431, (1999).

Speir, E., and Epstein, S.E., "Inhibition of Smooth Muscle Cell Proliferation by an Antisense Oligodeoxynucleotide Targeting the Messenger RNA Encoding Proliferating Cell Nuclear Antigen," Circulation, 862):538-547, (1992).

Stiernberg, J., et al., "The Role of Thrombin and Thrombin Receptor Activating Peptide (TRAP-508) in Initiation of Tissue Repair," Thrombosis and Haemostasis, 70(1):158-162, (1995).

Stiernberg, J., et al., "Acceleration of full-thickness wound healing in normal rats by the synthetic thrombin peptide, TP508," Wound Repair and Regeneration, 8(3):204-215, (2000).

Tsopanoglou, N.E., and Maragoudakis, M.E., "On the Mechanism of Thrombin-induced Angiogenesis," J. Biol. Chem., 274(34):23969-23976 (1999).

Voisard, R., et al., "High-dose diltiazem prevents migration and proliferation of vascular smooth muscle cells in various in-vitro models of human coronary restenosis," Coronary Artery Disease, 8(3/4):189-201, (1997).

* cited by examiner

RT-PCR
25 cycles eNOS — 425 bp
CTR  TNF  TP
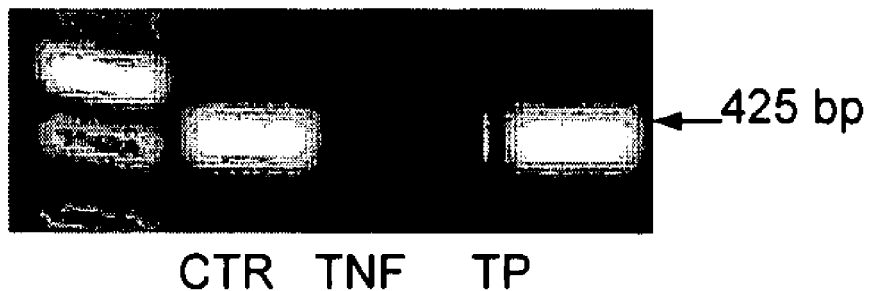
30 cycles eNOS — 425 bp
CTR  TNF  TP
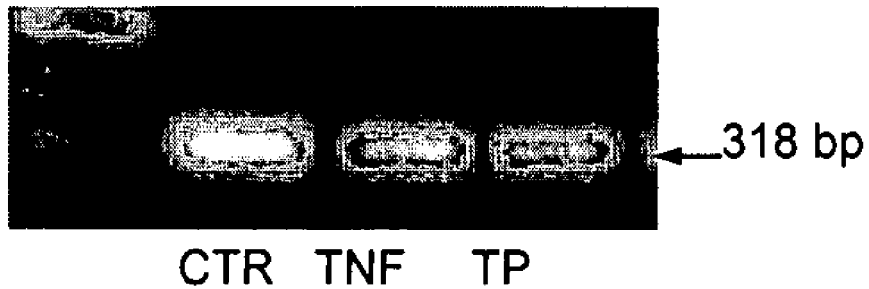
25 cycles 18S — 318 bp
CTR  TNF  TP
FIG. 5

MAHVRGLQLPGCLALAALCSLVHSQHVFLAPQQARSLLQRVRRA
NTFLEEVRKGNLERECVEETCSYEEAFGALESSTATDVFWAKYTACETARTPRDKLAA
CLEGNCAEGLGTNYRGHVNITRSGIECQLWRSRYPHKPEINSTTHPGADLQENFCRNP
DSSTTGPWCYTTDPTVRRQECSIPVCGQDQVTVAMTPRSEGSSVNLSPPLEQCVPDRG
QQYQGRLAVTTHGLPCLAWASAQAKALSKHQDFNSAVQLVENFCRNPDGDEEGVWCYV
AGKPGDFGYCDLNYCEEAVEEETGDGLDEDSDRAIEGRTATSEYQTFFNPRTFGSGEA
DCGLRPLFEKKSLEDKTERELLESYIDGRIVEGSDAEIGMSPWQVMLFRKSPQELLCG
ASLISDRWVLTAAHCLLYPPWDKNFTENDLLVRIGKHSRTRYERNIEKISMLEKIYIH
PRYNWRENLDRDIALMKLKKPVAFSDYIHPVCLPDRETAASLLQAGYKGRVTGWGNLK
ETWTANVGKGQPSVLQVVNLPIVERPVCKDSTRIRITDNMF<u>CAGYKPDEGKRGDACEG</u>
<u>DSGGPFVMKSPFNNRWYQMGIVSWGEGCDRDGKYGFYTHVFRLKKWIQKVIDQFGE</u>

FIG. 7

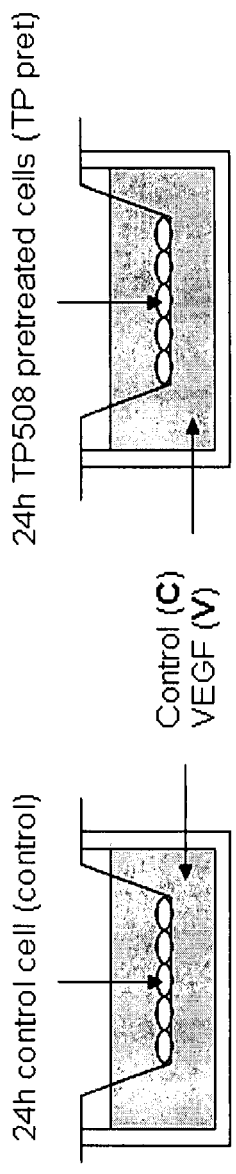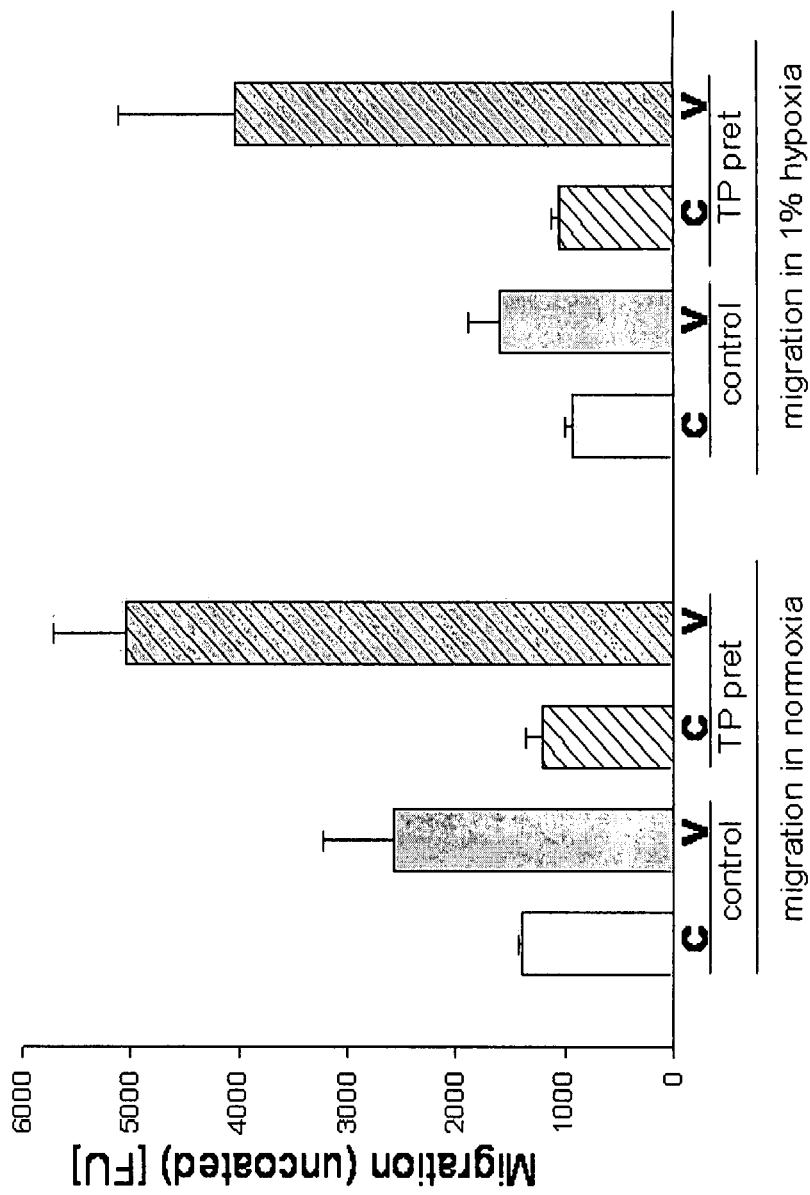
FIG. 9A
FIG. 9B

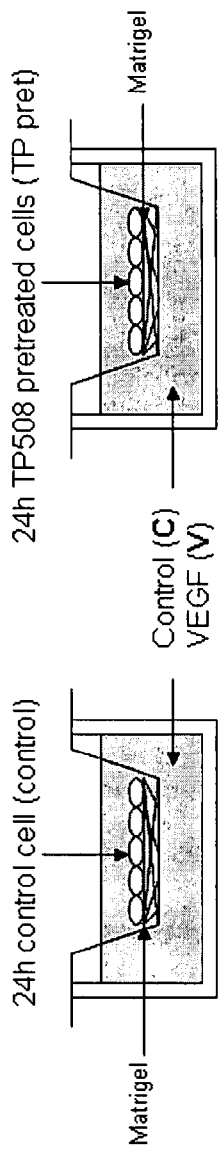
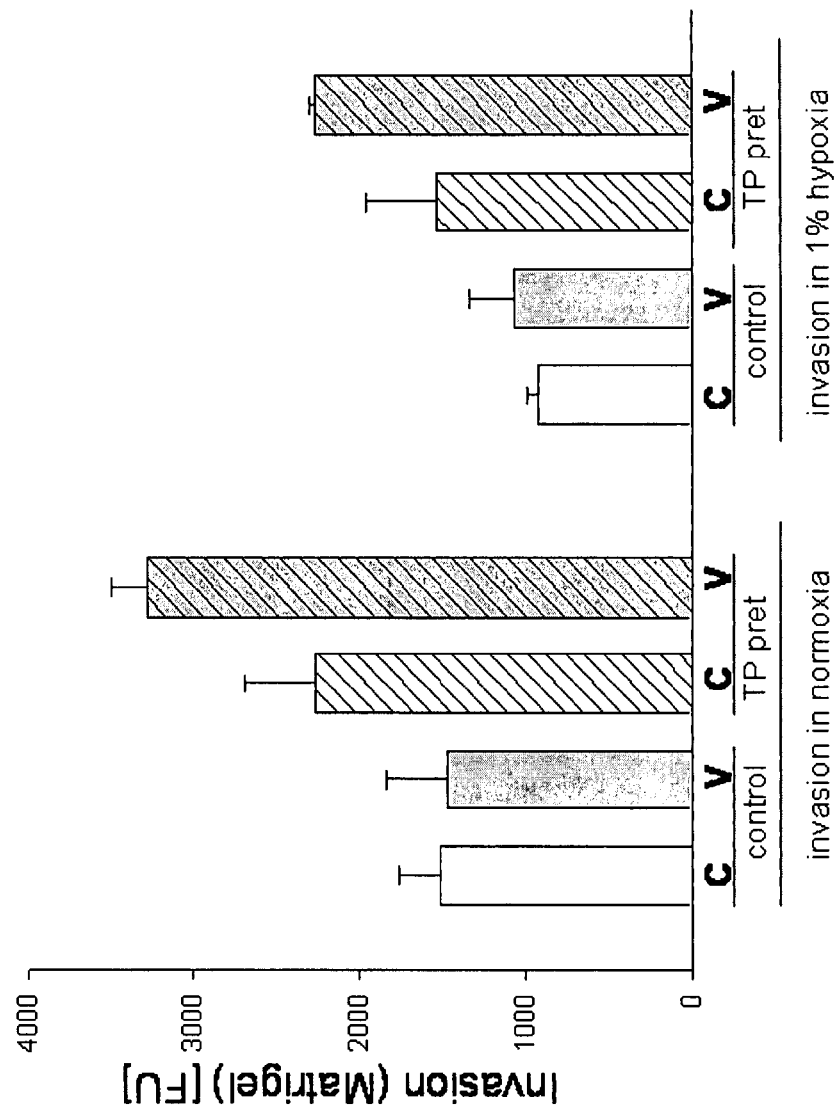
FIG. 10A
FIG. 10B

METHOD OF TREATING ENDOTHELIAL DYSFUNCTION COMPRISING ADMINISTRATION OF A THROMBIN PEPTIDE DERIVATIVE

RELATED APPLICATIONS

This application is the U.S. National Stage of International Application No. PCT/US2007/020445, which designated the United States and was filed 21 Sep. 2007, was published in English, and claims the benefit of U.S. Provisional Application No. 60/846,418 filed Sep. 22, 2006, U.S. Provisional Application No. 60/848,004 filed Sep. 28, 2006 and U.S. Provisional Application No. 60/922,646 filed Apr. 10, 2007. The entire teachings of the above applications are incorporated herein by reference.

BACKGROUND OF THE INVENTION

Vascular endothelial dysfunction (ED) is a common effect of aging and is associated with many diseases including hypertension, coronary artery disease, stroke, cerebrovascular disease, peripheral vascular disease, diabetes, erectile dysfunction, atherosclerosis, asthma, rheumatoid arthritis, pulmonary hypertension, hyperhomocysteinemia, sickle cell disease, pre-eclampsia, chronic renal failure, sepsis, and multiple organ failure. The ability of tissues to repair themselves in response to injury or ischemia or to respond to therapeutic intervention appears to be greatly diminished because of ED.

Endothelial dysfunction may be due to decreased expression of nitric oxide synthase (NOS), altered activation of pathways that block intracellular signaling events, increased levels of endogenous NOS inhibitors such as asymmetric dimethylarginine (ADMA), increased degradation or conversion of NO to peroxynitrites (due to high levels of reactive oxygen species) or increased activity of arginase which converts L-arginine to urea, thereby limiting the availability of L-arginine as a substrate for NOS.

A number of recent studies indicate that arginase plays a key role in ED and the modulation of NOS activity by regulating intracellular L-arginine availability. In aging vessels with ED, for example, arginase is upregulated, but addition of a specific arginase inhibitor restores endothelial function and nitric oxide (NO) responsiveness of vessels. Other diseases where arginase inhibition overcoming ED has been shown include asthma, where increased arginase activity contributes to a deficiency of NO and decreased airway smooth muscle relaxation, pulmonary hypertension, and spontaneous and salt-induced hypertension. L-arginine supplementation has also been shown to reverse ED completely or partially in a pig model of hypertension, in dilation defects caused by ischemia/reperfusion, and has even been shown to improve walking capability in patients with peripheral arterial disease. These studies suggest a potential therapeutic role for drugs that decrease arginase upregulation or control the activity of arginase in a number of vascular diseases.

Recent studies have shown that both hypoxia and certain inflammatory mediators, including TNFα, increase arginase or decrease endothelial cell nitric oxide synthase (eNOS) activity. Both prolonged inflammation and chronic ischemia appear to contribute to ED.

There is a need for methods to treat endothelial dysfunction, which is responsible for, or contributes to, a great many diseases and disorders.

SUMMARY OF THE INVENTION

Applicants have discovered that compounds which stimulate or activate the non-proteolytically activated thrombin receptor (hereinafter "NPAR") can reverse or inhibit endothelial dysfunction by blocking the up-regulation of arginase associated with endothelial dysfunction, and by promoting the activation or up-regulation of nitric oxide synthase, thereby increasing the production of nitric oxide. The NPAR agonist TP508 blocks the up-regulation of arginase 1 (ARG1) induced by TNFα (Example 2). The effect on ARG1 expression was shown to be dose dependent. TP508 treatment also increases phosphorylation of eNOS in cells cultured under normoxic (normal oxygen) and hypoxic (1% oxygen) conditions (Example 3). Moreover, TP508 stimulation of cells prevents hypoxia-induced down-regulation of eNOS expression, to maintain eNOS at a level that remains close to what would be observed in cells cultured under normoxic conditions. The effects of TP508 on eNOS phosphorylation are dose dependent.

The present invention is directed to methods of treating endothelial dysfunction at a site in a subject in need thereof, comprising administering to the subject a therapeutically effective amount of an NPAR agonist, wherein the site is not an artery injured by angioplasty, a chronic skin ulcer, a site in need of osteoinduction or a site in need of cardiac revascularization.

More specifically, the invention includes, with the exceptions as recited above, methods of treating endothelial dysfunction in a subject, wherein the subject is suffering from one or more diseases or conditions selected from the group consisting of hypertension, congestive heart failure, coronary artery disease, stroke, cerebrovascular disease, peripheral vascular disease, diabetes, erectile dysfunction, atherosclerosis, asthma, rheumatoid arthritis, pulmonary hypertension, acute lung injury, chronic obstructive pulmonary disease (COPD), cystic fibrosis, inflammatory lung disease, hyperhomocysteinemia, sickle cell disease, pre-eclampsia, chronic renal failure, chronic renal dysfunction, renal microvascular disease, hepatic reperfusion injury, neuropathy, Alzheimer's disease, thyroid disease, sepsis, thrombosis, multiple organ failure, inflammatory bowel disease, and radiation damage.

The present invention is also directed to methods of treating endothelial dysfunction at a site in a subject in need of treatment, comprising administering to the subject a combination in a therapeutically effective amount, the combination comprising one or more NPAR agonists and one or more angiogenic growth factors, wherein the site is not an artery injured by angioplasty, a chronic skin ulcer, a site in need of osteoinduction or a site in need of cardiac revascularization.

The invention is also a method of treating endothelial dysfunction at a site in a subject in need of treatment, comprising administering to the subject a combination in a therapeutically effective amount, the combination consisting essentially of an agonist of the non-proteolytically activated thrombin receptor and an angiogenic growth factor, wherein the site is not an artery injured by angioplasty, a chronic skin ulcer, a site in need of osteoinduction or a site in need of cardiac revascularization. In this method an angiogenic growth factor and an NPAR agonist are administered to the subject as the only therapeutically active agents in the combination therapy.

In some embodiments, the NPAR agonist can be administered to the subject systemically, and in other embodiments, can be administered vascularly, and in still other embodiments, can be administered locally or topically.

In one embodiment, the NPAR agonist is a thrombin peptide derivative disclosed herein. More specifically, one thrombin peptide derivative comprises the amino acid sequence of Arg-Gly-Asp-Ala-Cys-$X_1$-Gly-Asp-Ser-Gly-Gly-Pro-$X_2$-Val (SEQ ID NO:1), or a C-terminal truncated fragment thereof comprising at least six amino acids. In another specific embodiment, the thrombin peptide derivative comprises the amino acid sequence of SEQ ID NO:2: Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val, an N-terminal truncated fragment of the thrombin peptide derivative having at least fourteen amino acids, or a C-terminal truncated fragment of the thrombin peptide derivative comprising at least eighteen amino acids. $X_1$ is Glu or Gln and $X_2$ is Phe, Met, Leu, His or Val. In another specific embodiment, the thrombin peptide derivative is the polypeptide SEQ ID NO:3: H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (TP508).

In another embodiment, the NPAR agonist is a modified thrombin peptide derivative disclosed herein. In a specific embodiment, the modified thrombin peptide derivative comprises the amino acid sequence of SEQ ID NO:4: Arg-Gly-Asp-Ala-Xaa-$X_1$-Gly-Asp-Ser-Gly-Gly-Pro-$X_2$-Val, or a C-terminal truncated fragment thereof having at least six amino acids. In another specific embodiment, the modified thrombin peptide derivative comprises the amino acid sequence of SEQ ID NO:5: Ala-Gly-Tyr-Lys-Pro-Asp-Glu-Gly-Lys-Arg-Gly-Asp-Ala-Xaa-$X_1$-Gly-Asp-Ser-Gly-Gly-Pro-$X_2$-Val, or a fragment thereof comprising amino acids 10-18 of SEQ ID NO:5.

In another embodiment, the NPAR agonist is a thrombin peptide derivative dimer of two thrombin peptide derivatives disclosed herein. More specifically, a thrombin peptide derivative of a dimer comprises the amino acid sequence Arg-Gly-Asp-Ala-Cys-$X_1$-Gly-Asp-Ser-Gly-Gly-Pro-$X_2$-Val (SEQ ID NO:1) or a C-terminal truncated fragment thereof having at least six amino acids. In another specific embodiment, the thrombin peptide derivative of the dimer comprises a polypeptide having the amino acid sequence of SEQ ID NO:2: Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val, or a fragment thereof comprising amino acids 10-18 of SEQ ID NO:2. In another embodiment of the invention, the thrombin peptide derivative of the dimer is the polypeptide H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO:3). In another specific embodiment, the thrombin peptide derivative dimer is represented by the structural formula (IV).

In further embodiments, the NPAR agonist is an antibody or antigen-binding fragment thereof that binds to a complementary peptide, wherein the complementary peptide is encoded by the complement of a nucleotide sequence encoding a portion of thrombin.

The thrombin referred to above can be a mammalian thrombin, and in particular, a human thrombin. The portion of thrombin can be a thrombin receptor binding domain or a portion thereof. In one embodiment, the thrombin receptor binding domain or portion thereof comprises the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). Another portion of a thrombin receptor binding domain comprises the amino acid sequence Glu-Gly-Lys-Arg-Gly-Asp-Ala-Cys-Glu-Gly (SEQ ID NO:7).

The complementary peptide to which the antibody or the antigen-binding fragment thereof binds can be encoded by the 5'-3' sequence of the antisense RNA strand or encoded by the 3'-5' sequence of the antisense RNA strand.

In specific embodiments, the complementary peptide comprises the amino acid sequence Lys-Gly-Ser-Pro-Thr-Val-Thr-Phe-Thr-Gly-Ile-Pro-Cys-Phe-Pro-Phe-Ile-Arg-Leu-Val-Thr-Ser (SEQ ID NO:8) or Thr-Phe-Thr-Gly-Ile-Pro-Ser-Phe-Pro-Phe (SEQ ID NO:9) or Arg-Pro-Met-Phe-Gly-Leu-Leu-Pro-Phe-Ala-Pro-Leu-Arg-Thr-Leu-Pro-Leu-Ser-Pro-Pro-Gly-Lys-Gln (SEQ ID NO:10) or Lys-Pro-Phe-Ala-Pro-Leu-Arg-Thr-Leu-Pro (SEQ ID NO:11).

The NPAR agonist to be used in the methods of the invention can be a polyclonal antibody, or a monoclonal antibody or antigen-binding fragment thereof. In particular embodiments, these are human antibodies. Monoclonal antibodies to be used as NPAR agonists in methods of therapy can be humanized antibodies, chimeric antibodies or antigen-binding fragments of any of the foregoing, which can include Fab fragments, Fab' fragments, F(ab')$_2$ fragments and Fv fragments.

BRIEF DESCRIPTION OF THE DRAWINGS

FIG. 5 shows stained gels of products of RT-PCR from experiments designed to investigate the effect of TP508 on eNOS mRNA. Changes in eNOS mRNA expression in cells stimulated with TNFα or TP508 for 6 h were analyzed using RT-PCR.

FIG. 7 depicts the encoded amino acid sequence of human pro-thrombin (SEQ ID NO: 12). Amino acids 508-530, which contain the thrombin receptor binding domain, are underlined. Thrombin consists of the C-terminal 579 amino acid residues of prothrombin. See GenBank Accession No. AJ972449.

FIG. 9A is a diagram showing the experimental apparatus and design of experiments to measure migration of endothelial cells toward a chemoattractant.

FIG. 9B is a bar graph showing the effect of TP508 treatment on migration of endothelial cells toward the angiogenic factor VEGF.

FIG. 10A is a diagram showing the experimental apparatus and design of experiments to measure invasion of endothelial cells through Matrigel toward a chemoattractant.

FIG. 10B is a bar graph showing the effect of TP508 treatment on invasion of endothelial cells toward the angiogenic factor VEGF.

FIGS. 13A-13B show endothelium-dependent NOmediated vasodilation. The degree of endothelial dysfunction was evaluated in arterioles isolated from normoxic control left anterior descending artery (Nonischemic) or ischemic left circumflex coronary artery of placebo (Ischemic placebo) or TP508-treated (Ischemic TP508) hearts by determining the degree of vasodilation as a percentage of maximal dilation in response to indicated concentrations of adenosine (FIG. 13A) or serotonin (FIG. 13B). *$p<0.05$ compared with nonischemic; #$p<0.05$ compared with ischemic placebo. FIGS. 13C and 13D show endothelium-independent NOmediated vasodilation. To determine potential effects of ischemia and TP508 on NO-independent vasodilation, isolated arterioles were stimulated with the indicated concentrations of nitroprusside (FIG. 13C) or pinacidil (FIG. 13D).

DETAILED DESCRIPTION OF THE INVENTION

Figure 1:
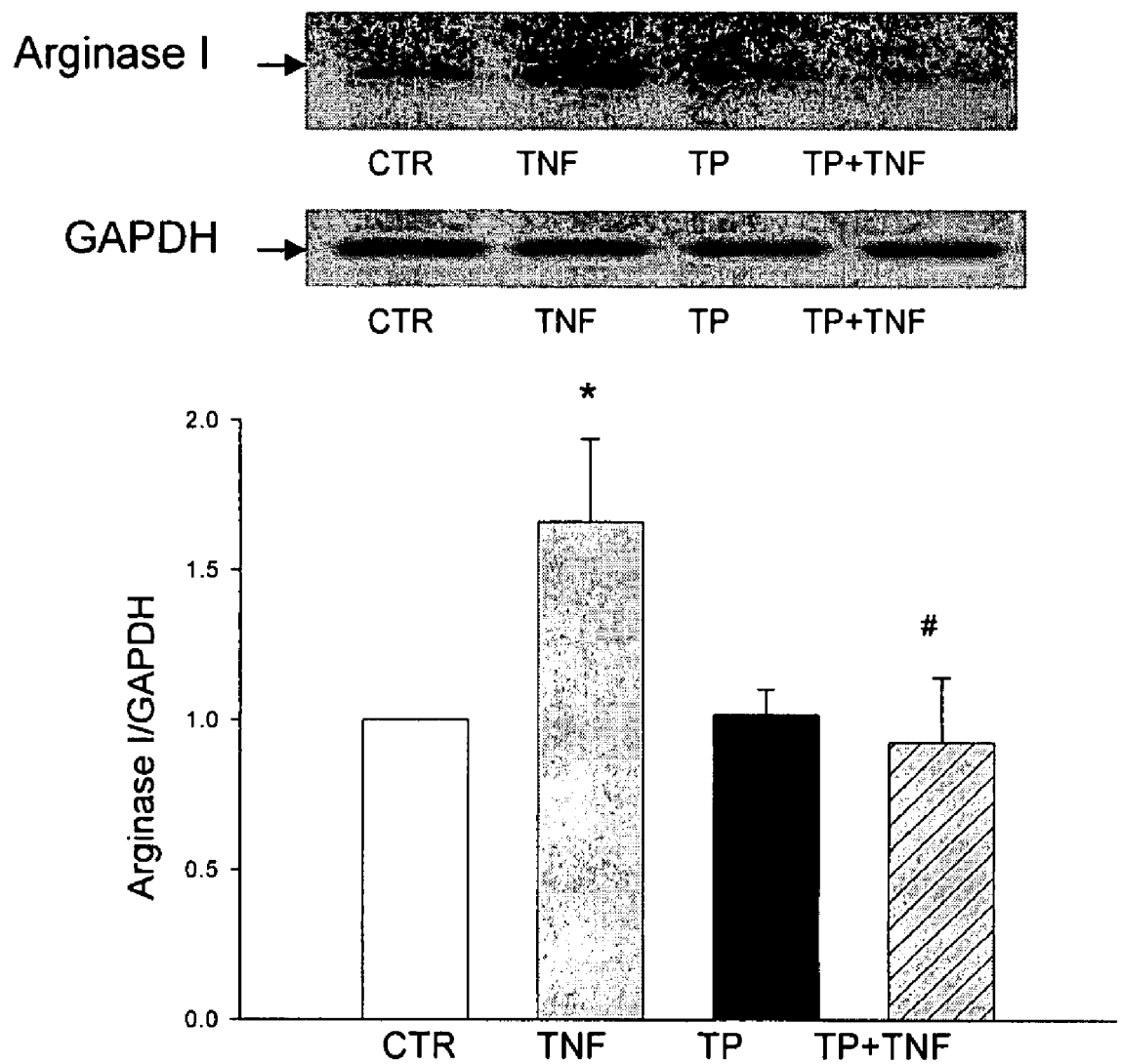
FIG. 1 shows X-ray films from a representative western blot and a corresponding bar graph of ratios of densitometry readings from the bands on western blots from experiments examining the effect of TP508 on expression levels of arginase 1 in cells cultured with or without TNFα. Human coronary artery endothelial (HCAE) cells were incubated in the absence (CTR) or presence of TP508 (TP) for 1 h prior to treatment with TNFα for 24 h. Cell lysates were analyzed for human arginase 1 expression by immunoblotting using antibody specific for this enzyme. After stripping, the membrane was reprobed with GAPDH antibody to show protein loading. (Glyceraldehyde-3-phosphate dehydrogenase (GAPDH) levels are unaffected by TNFα or hypoxia.) Corresponding densitometric data represent the mean±SD of 4 independent experiments [$p<0.05$; CTR vs. TNFα (*) or TNFα vs. TP+TNFα (#)].

Endothelial dysfunction has been implicated in the etiology of a variety of diseases including hypertension, congestive heart failure, coronary artery disease, stroke, cerebrovascular disease, peripheral vascular disease, diabetes, erectile dysfunction, atherosclerosis, asthma, rheumatoid arthritis, pulmonary hypertension, acute lung injury, chronic obstructive pulmonary disease (COPD), cystic fibrosis, inflammatory lung disease, hyperhomocysteinemia, sickle cell disease, pre-eclampsia, chronic renal failure, chronic renal dysfunction, renal microvascular disease, hepatic reperfusion injury, neuropathy, Alzheimer's disease, thyroid disease, sepsis, thrombosis, multiple organ failure, inflammatory bowel disease, and radiation damage.

Applicants have discovered that compounds which stimulate or activate the non-proteolytically activated thrombin receptor (hereinafter "NPAR") can reverse or inhibit endothelial dysfunction by blocking the up-regulation of arginase associated with endothelial dysfunction and by promoting the activation or up-regulation of nitric oxide synthase, thereby increasing the production of nitric oxide. TP508 blocks the up-regulation of arginase induced by TNFα. The effect is dose dependent. TP508 treatment also increases phosphorylation of eNOS in cells cultured under normoxic (normal oxygen) and hypoxic (1% oxygen) conditions. Moreover, TP508 stimulation of cells prevents hypoxia-induced down-regulation of eNOS expression, to maintain eNOS at a level that remains close to what would be observed in cells cultured under normoxic conditions. The effects of TP508 on eNOS phosphorylation are dose dependent (Example 3).

The invention includes methods of treating endothelial dysfunction, and methods of treating the consequences of endothelial dysfunction, at a site in a subject in need thereof, comprising administering to the subject a therapeutically effective amount of an agonist of the non-proteolytically activated thrombin receptor, wherein the site is not an artery injured by angioplasty, a chronic skin ulcer, a site in need of osteoinduction or a site in need of cardiac revascularization. In particular embodiments, the subject to be treated is suffering from or has suffered from one or more disease(s) selected from the group consisting of hypertension, congestive heart failure, coronary artery disease, stroke, cerebrovascular disease, peripheral vascular disease, diabetes, erectile dysfunction, atherosclerosis, asthma, rheumatoid arthritis, pulmonary hypertension, acute lung injury, chronic obstructive pulmonary disease (COPD), cystic fibrosis, inflammatory lung disease, hyperhomocysteinemia, sickle cell disease, pre-eclampsia, chronic renal failure, chronic renal dysfunction, renal microvascular disease, hepatic reperfusion injury, neuropathy, Alzheimer's disease, thyroid disease, sepsis, thrombosis, multiple organ failure, inflammatory bowel disease, and radiation damage.

In a particular aspect, the invention is a method of treating endothelial dysfunction, thereby treating impaired glucose tolerance in a subject, comprising administering to the subject a therapeutically effective amount of an agonist of the non-proteolytically activated thrombin receptor. Subjects with impaired glucose intolerance include those at risk of developing type 2 diabetes. In another aspect, the invention is a method of treating endothelial dysfunction, thereby treating the complications of diabetes in a subject, comprising administering to the subject a therapeutically effective amount of an agonist of the non-proteolytically activated thrombin receptor. In these aspects, the subject is not in need of treatment at a site which is an artery injured by angioplasty, a chronic skin ulcer, a site in need of osteoinduction or a site in need of cardiac revascularization.

In another aspect, the invention is a method of treating atherosclerosis in a subject, comprising administering to the subject a therapeutically effective amount of an agonist of the non-proteolytically activated thrombin receptor. In this aspect, the subject is not in need of treatment at a site which is an artery injured by angioplasty, a chronic skin ulcer, a site in need of osteoinduction or a site in need of cardiac revascularization.

Endothelial dysfunction is a cause of toxicity from ionizing radiation. In the irradiated gut, for example, endothelial cells are depleted, leading to breakdown of the mucosal barrier, which, in turn, leads to inflammation, the production of reactive oxygen species, and the release of signaling molecules such as TGF-β and TNF-α. Among the effects of this inflammatory reaction are a decrease in crypt cell proliferation, mucositis and secretory diarrhea, and increases in mesenchymal cell proliferation and collagen production, leading to fibrosis and scarring. A subject can suffer damage from ionizing radiation following high doses of therapeutic radiation as treatment for various forms of cancer, or in case of radiation exposure from an industrial accident, for example.

In still another aspect, the invention is a method of treating radiation damage in a subject, comprising administering to the subject a therapeutically effective amount of an agonist of the non-proteolytically activated thrombin receptor. In this aspect, the subject is not in need of treatment at a site which is an artery injured by angioplasty, a chronic skin ulcer, a site in need of osteoinduction or a site in need of cardiac revascularization.

NPAR Agonists

Compounds which stimulate NPAR are said to be NPAR agonists. NPAR is a high-affinity thrombin receptor present on the surface of most cells. This NPAR component is largely responsible for high-affinity binding of thrombin, proteolytically inactivated thrombin, and thrombin derived peptides to cells. NPAR appears to mediate a number of cellular signals that are initiated by thrombin independent of its proteolytic activity. An example of one such signal is the upregulation of annexin V and other molecules identified by subtractive hybridization (see Sower, et. al., *Experimental Cell Research* 247:422 (1999)). NPAR is therefore characterized by its high affinity interaction with thrombin at cell surfaces and its activation by proteolytically inactive derivatives of thrombin and thrombin derived peptide agonists as described below. NPAR activation can be assayed based on the ability of molecules to stimulate cell proliferation when added to fibroblasts in the presence of submitogenic concentrations of thrombin or molecules that activate protein kinase C, as disclosed in U.S. Pat. Nos. 5,352,664 and 5,500,412. The entire teachings of these patents are incorporated herein by reference. NPAR agonists can be identified by this activation or by their ability to compete with $^{125}$I-thrombin binding to cells.

A thrombin receptor binding domain is defined as a polypeptide or portion of a polypeptide which directly binds to the thrombin receptor and/or competitively inhibits binding between high-affinity thrombin receptors and alpha-thrombin.

NPAR agonists of the present invention include thrombin derivative peptides, modified thrombin derivative peptides, thrombin derivative peptide dimers and NPAR agonist antibodies to complementary peptides of thrombin as disclosed herein.

Thrombin Derivative Peptides

Among NPAR agonists are thrombin peptide derivatives (also: "thrombin derivative peptides"), which are analogs of thrombin that have an amino acid sequence derived at least in part from that of thrombin and are active at the non-proteolytically activated thrombin receptor. Thrombin peptide derivatives include, for example, peptides that are produced by recombinant DNA methods, peptides produced by enzymatic digestion of thrombin, and peptides produced synthetically, which can comprise amino acid substitutions compared to thrombin and/or modified amino acids, especially at the termini.

NPAR agonists of the present invention include thrombin derivative peptides described in U.S. Pat. Nos. 5,352,664 and 5,500,412. In one embodiment, the NPAR agonist of the present invention is a thrombin peptide derivative or a physiologically functional equivalent, i.e., a polypeptide with no more than about fifty amino acids, preferably no more than about thirty amino acids and having sufficient homology to the fragment of human thrombin corresponding to thrombin amino acids 508-530 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val; SEQ ID NO:6) that the polypeptide activates NPAR. The thrombin peptide derivatives or modified thrombin peptide derivatives described herein preferably have from about 12 to about 23 amino acid residues, more preferably from about 19 to about 23 amino acid residues.

In another embodiment, the NPAR agonist of the present invention is a thrombin peptide derivative comprising a moiety represented by Structural Formula (I):

Asp-Ala-R     (I).

R is a serine esterase conserved domain. Serine esterases, e.g., trypsin, thrombin, chymotrypsin and the like, have a region that is highly conserved. "Serine esterase conserved domain" refers to a polypeptide having the amino acid sequence of one of these conserved regions or is sufficiently homologous to one of these conserved regions such that the thrombin peptide derivative retains NPAR activating ability.

A physiologically functional equivalent of a thrombin derivative encompasses molecules which differ from thrombin derivatives in particulars which do not affect the function of the thrombin receptor binding domain or the serine esterase conserved amino acid sequence. Such particulars may include, but are not limited to, conservative amino acid substitutions (as defined below for NPAR agonists) and modifications, for example, amidation of the carboxyl terminus, acetylation of the amino terminus, conjugation of the polypeptide to a physiologically inert carrier molecule, or sequence alterations in accordance with the serine esterase conserved sequences.

A domain having a serine esterase conserved sequence can comprise a polypeptide sequence containing at least 4-12 of the N-terminal amino acids of the dodecapeptide previously shown to be highly conserved among serine proteases (Asp-X$_1$-Cys-X$_2$-Gly-Asp-Ser-Gly-Gly-Pro-X$_3$-Val; SEQ ID NO:13); wherein X$_1$ is either Ala or Ser; X$_2$ is either Glu or Gln; and X$_3$ is Phe, Met, Leu, His, or Val).

In one embodiment, the serine esterase conserved sequence comprises the amino acid sequence of SEQ ID NO:14 (Cys-Glu-Gly-Asp-Ser-Gly-Gly-Pro-Phe-Val) or a C-terminal truncated fragment of a polypeptide having the amino acid sequence of SEQ ID NO:14. It is understood, however, that zero, one, two or three amino acids in the serine esterase conserved sequence can differ from the corresponding amino acid in SEQ ID NO:14. Preferably, the amino acids in the serine esterase conserved sequence which differ from the corresponding amino acid in SEQ ID NO:14 are conservative substitutions as defined below, and are more preferably highly conservative substitutions. A "C-terminal truncated fragment" refers to a fragment remaining after removing an amino acid or block of amino acids from the C-terminus, said fragment having at least six and more preferably at least nine amino acids.

In another embodiment, the serine esterase conserved sequence comprises the amino acid sequence of SEQ ID NO:15 (Cys-X$_1$-Gly-Asp-Ser-Gly-Gly-Pro-X$_2$-Val; X$_1$ is Glu or Gln and X$_2$ is Phe, Met, Leu, His or Val) or a C-terminal truncated fragment thereof having at least six amino acids, preferably at least nine amino acids.

In a preferred embodiment, the thrombin peptide derivative comprises a serine esterase conserved sequence and a polypeptide having a more specific thrombin amino acid sequence Arg-Gly-Asp-Ala (SEQ ID NO:16). One example of a thrombin peptide derivative of this type comprises Arg-Gly-Asp-Ala-Cys-X$_1$-Gly-Asp-Ser-Gly-Gly-Pro-X$_2$-Val (SEQ ID NO:1). X$_1$ and X$_2$ are as defined above. The thrombin peptide derivative can comprise the amino acid sequence of SEQ ID NO:6 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val) or an N-terminal truncated fragment thereof, provided that zero, one, two or three amino acids at positions 1-9 in the thrombin peptide derivative differ from the amino acid at the corresponding position of SEQ ID NO:6. Preferably, the amino acid residues in the thrombin peptide derivative which differ from the corresponding amino acid residues in SEQ ID NO:6 are conservative substitutions as defined below for NPAR agonists, and are more preferably highly conservative substitutions. An "N-terminal truncated fragment" refers to a fragment remaining after removing an amino acid or block of amino acids from the N-terminus, preferably a block of no more than six amino acids, more preferably a block of no more than three amino acids.

Optionally, the thrombin peptide derivatives described herein can be amidated at the C-terminus and/or acylated at the N-terminus. In a specific embodiment, the thrombin peptide derivatives comprise a C-terminal amide and optionally comprise an acylated N-terminus, wherein said C-terminal amide is represented by —C(O)NR$_a$R$_b$, wherein R$_a$ and R$_b$ are independently hydrogen, a C$_1$-C$_{10}$ substituted or unsubstituted aliphatic group, or R$_a$ and R$_b$, taken together with the nitrogen to which they are bonded, form a C$_1$-C$_{10}$ non-aromatic heterocyclic group, and said N-terminal acyl group is represented by R$_c$C(O)—, wherein R$_c$ is hydrogen, a C$_1$-C$_{10}$ substituted or unsubstituted aliphatic group, or a C$_1$-C$_{10}$ substituted or unsubstituted aromatic group. In another specific embodiment, the N-terminus of the thrombin peptide derivative is free (i.e., unsubstituted) and the C-terminus is free (i.e., unsubstituted) or amidated, preferably as a carboxamide (i.e., —C(O)NH$_2$). In a specific embodiment, the thrombin peptide derivative comprises the following amino acid sequence: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). In another specific embodiment, the thrombin peptide derivative comprises the amino sequence of Arg-Gly-Asp-Ala-Cys-Glu-Gly-Asp-Ser-Gly-Gly-Pro-Phe-Val (SEQ ID NO:17). Alternatively, the thrombin peptide derivative comprises the amino acid sequence of SEQ ID NO:18: Asp-Asn-Met-Phe-Cys-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe. The thrombin peptide derivates comprising the amino acids of SEQ ID NO: 6, 17, or 18 can optionally be amidated at the C-terminus and/or acylated at the N-terminus. Preferably, the N-terminus is free (i.e., unsubstituted) and the C-terminus is free (i.e., unsubstituted) or amidated, preferably a carboxamide (i.e., —C(O)NH$_2$). It is understood, however, that zero, one, two or three amino acids at positions 1-9 and 14-23 in the thrombin peptide derivative can differ from the corresponding amino acid in SEQ ID NO:6. It is also understood that zero, one, two or three amino acids at positions 1-14 and 19-33 in the thrombin peptide derivative can differ from the corresponding amino acid in SEQ ID NO:18. Preferably, the amino acids in the thrombin peptide derivative which differ from the corresponding amino acid in SEQ ID NO:6 or SEQ ID NO:18 are conservative substitutions as defined below, and are more preferably highly conservative substitutions. Alternatively, an N-terminal truncated fragment of the thrombin peptide derivative having at least fourteen amino acids or a C-terminal truncated fragment of the thrombin peptide derivative having at least eighteen amino acids is a thrombin peptide derivative to be used as an NPAR agonist.

A "C-terminal truncated fragment" refers to a fragment remaining after removing an amino acid or block of amino acids from the C-terminus. An "N-terminal truncated fragment" refers to a fragment remaining after removing an amino acid or block of amino acids from the N-terminus. It is to be understood that the terms "C-terminal truncated fragment" and "N-terminal truncated fragment" encompass acylation at the N-terminus and/or amidation at the C-terminus, as described above.

A preferred thrombin peptide derivative for use in the disclosed method comprises the amino acid sequence SEQ ID NO:2: Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val.

Another preferred thrombin peptide derivative for use in the disclosed method comprises the amino acid sequence of SEQ ID NO:19: Asp-Asn-Met-Phe-Cys-Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val-Met-Lys-Ser-Pro-Phe. X$_1$ is Glu or Gln; X$_2$ is Phe, Met, Leu, His or Val. The thrombin peptide derivatives of SEQ ID NO:2 and SEQ ID NO:19 can optionally comprise a C-terminal amide and/or acylated N-terminus, as defined above. Preferably, the N-terminus is free (i.e., unsubstituted) and the C-terminus is free (i.e., unsubstituted) or amidated, preferably as a carboxamide (i.e., —C(O)NH$_2$). Alternatively, N-terminal truncated fragments of these preferred thrombin peptide derivatives, the N-terminal truncated fragments having at least fourteen amino acids, or C-terminal truncated fragments of these preferred thrombin peptide derivatives, the C-terminal truncated fragments having at least eighteen amino acids, can also be used in the disclosed method.

TP508 is an example of a thrombin peptide derivative and is 23 amino acid residues long, wherein the N-terminal amino acid residue Ala is unsubstituted and the COOH of the C-terminal amino acid Val is modified to an amide represented by —C(O)NH$_2$ (SEQ ID NO:3). Another example of a thrombin peptide derivative comprises the amino acid sequence of SEQ ID NO:6, wherein both N- and C-termini are unsubstituted ("deamide TP508"). Other examples of thrombin peptide derivatives which can be used in the disclosed method include N-terminal truncated fragments of TP508 (or deamide TP508), the N-terminal truncated fragments having at least fourteen amino acids, or C-terminal truncated fragments of TP508 (or deamide TP508), the C-terminal truncated fragments having at least eighteen amino acids.

As used herein, a "conservative substitution" in a polypeptide is the replacement of an amino acid with another amino acid that has the same net electronic charge and approximately the same size and shape. Amino acids with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

As used herein, a "highly conservative substitution" in a polypeptide is the replacement of an amino acid with another amino acid that has the same functional group in the side chain and nearly the same size and shape. Amino acids with aliphatic or substituted aliphatic amino acid side chains have nearly the same size when the total number of carbon and heteroatoms in their side chains differs by no more than two. They have nearly the same shape when they have the same number of branches in the their side chains. Examples of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

Modified Thrombin Peptide Derivatives

In one embodiment of the invention, the NPAR agonists are modified relative to the thrombin peptide derivatives described above, wherein cysteine residues of aforementioned thrombin peptide derivatives are replaced with amino acids having similar size and charge properties to minimize dimerization of the peptides. Examples of suitable amino acids include alanine, glycine, serine, or an S-protected cysteine. Preferably, cysteine is replaced with alanine. The modified thrombin peptide derivatives have about the same biological activity as the unmodified thrombin peptide derivatives. See Publication No. US 2005/0158301 A1, which is hereby incorporated by reference.

It will be understood that the modified thrombin peptide derivatives disclosed herein can optionally comprise C-terminal amides and/or N-terminal acyl groups, as described above. Preferably, the N-terminus of a thrombin peptide derivative is free (i.e., unsubstituted) and the C-terminus is free (i.e., unsubstituted) or amidated, preferably as a carboxamide (i.e., —C(O)NH$_2$).

In a specific embodiment, the modified thrombin peptide derivative comprises a polypeptide having the amino acid sequence of SEQ ID NO:4: Arg-Gly-Asp-Ala-Xaa-X$_1$-Gly-Asp-Ser-Gly-Gly-Pro-X$_2$-Val, or a C-terminal truncated fragment thereof having at least six amino acids. More specifically, the thrombin peptide derivative comprises the amino acid sequence of SEQ ID NO:20: Ala-Gly-Tyr-Lys-Pro-Asp-Glu-Gly-Lys-Arg-Gly-Asp-Ala-Xaa-Glu-Gly-Asp-Ser-Gly-Gly-Pro-Phe-Val or a fragment thereof comprising amino acids 10-18 of SEQ ID NO:20. Even more specifically, the thrombin peptide derivative comprises the amino acid sequence SEQ ID NO:5: Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val, or a fragment thereof comprising amino acids 10-18 of SEQ ID NO:5. Xaa is alanine, glycine, serine or an S-protected cysteine. X$_1$ is Glu or Gln and X$_2$ is Phe, Met, Leu, His or Val. Preferably X$_1$ is Glu, X$_2$ is Phe, and Xaa is alanine. One example of a thrombin peptide derivative of this type is a polypeptide having the amino acid sequence Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val (SEQ ID NO:21). A further example of a thrombin peptide derivative of this type is the polypeptide H-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-NH$_2$ (SEQ ID NO:22). Zero, one, two or three amino acids in the thrombin peptide derivative differ from the amino acid at the corresponding position of SEQ ID NO:4, 20, 5, 21 or 22, provided that Xaa is alanine, glycine, serine or an S-protected cysteine. Preferably, the difference is conservative as defined for conservative substitutions of NPAR agonists.

In another specific embodiment, the thrombin peptide derivative comprises a polypeptide having the amino acid sequence SEQ ID NO:23: Asp-Asn-Met-Phe-Xbb-Ala-Gly-Tyr-Lys-Pro-Asp-Glu-Gly-Lys-Arg-Gly-Asp-Ala-Xaa-Glu-Gly-Asp-Ser-Gly-Gly-Pro-Phe-Val-Met-Lys-Ser-Pro-Phe, or a fragment thereof comprising amino acids 6-28. More preferably, the thrombin peptide derivative comprises a polypeptide having the amino acid sequence SEQ ID NO:24: Asp-Asn-Met-Phe-Xbb-Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val-Met-Lys-Ser-Pro-Phe, or a fragment thereof comprising amino acids 6-28. Xaa and Xbb are independently alanine, glycine, serine or an S-protected cysteine. X$_1$ is Glu or Gln and X$_2$ is Phe, Met, Leu, His or Val. Preferably X$_1$ is Glu, X$_2$ is Phe, and Xaa and Xbb are alanine. One example of a thrombin peptide derivative of this type is a polypeptide comprising the amino acid sequence Asp-Asn-Met-Phe-Ala-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-Met-Lys-Ser-Pro-Phe (SEQ ID NO:25). A further example of a thrombin peptide derivative of this type is the polypeptide H-Asp-Asn-Met-Phe-Ala-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-Met-Lys-Ser-Pro-Phe-NH$_2$ (SEQ ID NO:26). Zero, one, two or three amino acids in the thrombin peptide derivative can differ from the amino acid at the corresponding position of SEQ ID NO:23, 24, 25 or 26. Xaa and Xbb are independently alanine, glycine, serine or an S-protected cysteine. Preferably, the difference is conservative as in conservative substitutions of NPAR agonists.

An "S-protected cysteine" is a cysteine residue in which the reactivity of the thiol moiety, —SH, is blocked with a protecting group. Suitable protecting groups are known in the art and are disclosed, for example, in T. W. Greene and P. G. M. Wuts, *Protective Groups in Organic Synthesis*, 3$^{rd}$ Edition, John Wiley & Sons, (1999), pp. 454-493, the teachings of which are incorporated herein by reference in their entirety. Suitable protecting groups should be non-toxic, stable in pharmaceutical formulations and have minimum additional functionality to maintain the activity of the thrombin peptide derivative. A free thiol can be protected as a thioether, a thioester, or can be oxidized to an unsymmetrical disulfide. Preferably the thiol is protected as a thioether. Suitable thioethers include, but are not limited to, S-alkyl thioethers (e.g., C$_1$-C$_5$ alkyl), and S-benzyl thioethers (e.g., cysteine-S—S-t-Bu). Preferably the protective group is an alkyl thioether. More preferably, the S-protected cysteine is an S-methyl cysteine. Alternatively, the protecting group can be: 1) a cysteine or a cysteine-containing peptide (the "protecting peptide") attached to the cysteine thiol group of the thrombin peptide derivative by a disulfide bond; or 2) an amino acid or peptide ("protecting peptide") attached by a thioamide bond between the cysteine thiol group of the thrombin peptide derivative and a carboxylic acid in the protecting peptide (e.g., at the C-terminus or side chain of aspartic acid or glutamic acid). The protecting peptide can be physiologically inert (e.g., a polyglycine or polyalanine of no more than about fifty amino acids optionally interrupted by a cysteine), or can have a desirable biological activity.

Thrombin Peptide Derivative Dimers

In some aspects of the present invention, the NPAR agonists of the methods are thrombin peptide derivative dimers. See Publication No. US 2005/0153893, which is hereby incorporated by reference. The dimers essentially do not revert to monomers and still have about the same biological activity as the thrombin peptide derivatives monomer described above. A "thrombin peptide derivative dimer" is a molecule comprising two thrombin peptide derivatives linked by a covalent bond, preferably a disulfide bond between cysteine residues. Thrombin peptide derivative dimers are typically essentially free of the corresponding monomer, e.g., greater than 95% free by weight and preferably greater than 99% free by weight. Preferably the polypeptides are the same and covalently linked through a disulfide bond.

The thrombin peptide derivative dimers of the present invention comprises the thrombin peptide derivatives described above. Specifically, thrombin peptide derivatives have less than about fifty amino acids, preferably less than about thirty-three amino acids. Thrombin peptide derivatives also have sufficient homology to the fragment of human thrombin corresponding to thrombin amino acid residues 508-530: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6) so that the polypeptide activates NPAR. The thrombin peptide derivative dimers described herein are formed from polypeptides typically having at least six amino acids and preferably from about 12 to about 33 amino acid residues, and more preferably from about 12 to about 23 amino acid residues.

In a specific embodiment, each thrombin peptide derivative comprising a dimer comprises a polypeptide having the amino acid sequence SEQ ID NO:1: Arg-Gly-Asp-Ala-Cys-$X_1$-Gly-Asp-Ser-Gly-Gly-Pro-$X_2$-Val, or a C-terminal truncated fragment thereof comprising at least six amino acids. More specifically, each thrombin peptide derivative comprises the amino acid sequence of SEQ ID NO:6: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val, or a fragment thereof comprising amino acids 10-18 of SEQ ID NO. 5. Even more specifically, the thrombin peptide derivative comprises the amino acid sequence SEQ ID NO:2: Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val, or a fragment thereof comprising amino acids 10-18 of SEQ ID NO:2. $X_1$ is Glu or Gln and $X_2$ is Phe, Met, Leu, His or Val. Preferably $X_1$ is Glu, and $X_2$ is Phe. One example of a thrombin peptide derivative of this type is a polypeptide comprising the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). A further example of a thrombin peptide derivative of this type is a polypeptide having the amino acid sequence H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:3). Zero, one, two or three amino acids in the thrombin peptide derivative differ from the amino acid at the corresponding position of SEQ ID NO:6, 1, 2, or 3. Preferably, the difference is conservative as for conservative substitutions of NPAR agonists.

One example of a thrombin peptide derivative dimer of the present invention is represented by Formula (IV):

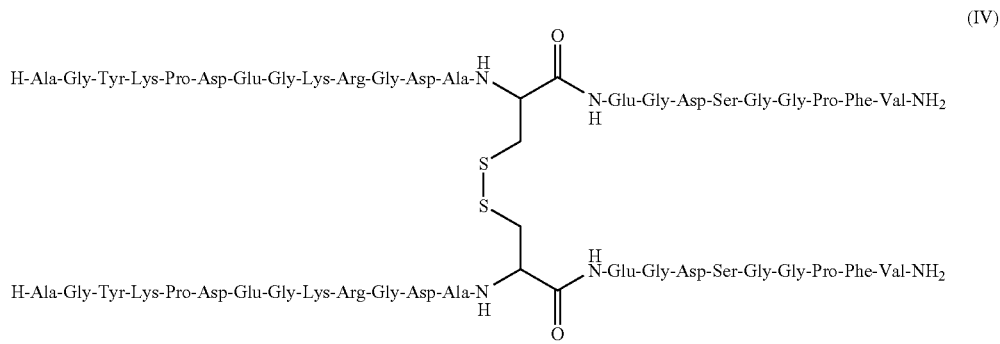

(IV)

In another specific embodiment, each thrombin peptide derivative comprising a dimer comprises a polypeptide comprising the amino acid sequence SEQ ID NO:27: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr, or a C-terminal truncated fragment thereof having at least twenty-three amino acids. More preferably, each thrombin peptide derivative comprises the amino acid sequence SEQ ID NO:28: Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val-Met-Lys-Ser-Pro-Phe-Asn-Asn-Arg-Trp-Tyr, or a C-terminal truncated fragment thereof comprising at least twenty-three amino acids. $X_1$ is Glu or Gln and $X_2$ is Phe, Met, Leu, His or Val. Preferably $X_1$ is Glu, and $X_2$ is Phe. One example of a thrombin peptide derivative of this type is a polypeptide comprising the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr (SEQ ID NO:27). A further example of a thrombin peptide derivative of this type is a polypeptide comprising the amino acid sequence H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr-NH$_2$ (SEQ ID NO:29). Zero, one, two or three amino acids in the thrombin peptide derivative differ from the amino acid at the corresponding position of SEQ ID NO:27, 28 or 29. Preferably, the difference is conservative as defined for conservative substitutions of NPAR agonists.

NPAR Agonist Antibodies

A particular class of NPAR agonists includes antibodies and antigen-binding fragments that can both bind to and activate the non-proteolytically activated thrombin receptor (NPAR), and can bind to one or more complementary peptides as described below. Agonist antibodies that bind to thrombin receptors have been described in the art. For example, Frost et al. teach that a monoclonal antibody, TR-9, can mimic the effects of thrombin's high affinity interaction with the high affinity thrombin receptor (Frost, G. H., et al., J. Cell Biol. 105 (6 PT. 1):2551-58 (1987)).

Antibodies or antigen-binding fragments thereof that are NPAR agonists can be found by their binding to a complementary peptide that is encoded by the complement of a nucleotide sequence encoding a portion of thrombin. See *Molecular Recognition Theory* below. In one instance, the NPAR agonist antibody or antigen-binding fragment binds to a complementary peptide that is encoded by the complement of a nucleotide sequence encoding a portion of thrombin. In another instance, the NPAR agonist antibody or antigen-binding fragment can be found by its binding to a complementary peptide that is encoded by the complement of a nucleotide sequence encoding a portion of thrombin. In one embodiment, the thrombin or portion thereof (which is encoded by the sense or +RNA strand and is the complement of the RNA strand encoding the complementary peptide to which the antibody or antigen-binding fragment binds) is a mammalian thrombin or a portion of a mammalian thrombin. In another embodiment, the thrombin or portion thereof is a human thrombin or a portion of a human thrombin.

Antibodies or antigen-binding fragments thereof that bind to a complementary peptide, wherein the complementary peptide is encoded by the complement of a nucleotide sequence encoding thrombin or a portion thereof, can be NPAR agonists. In one embodiment, the portion of thrombin (which is encoded by the sense or +RNA strand and is the complement of the RNA strand encoding the complementary peptide to which the antibody or antigen-binding fragment binds) is a thrombin receptor binding domain or a portion thereof. As used herein, a thrombin receptor binding domain or a portion thereof is a segment of thrombin that is capable of selectively binding to the high-affinity non-proteolytically activated thrombin receptor (NPAR). Such thrombin receptor binding domains contain a portion of a domain (represented by amino acid residues 517-520 of human thrombin; see FIG. 7 depicting the amino acid sequence of human prothrombin (SEQ ID NO:12) with a sequence homologous to the tripeptide cell binding domain of fibronectin, Arg-Gly-Asp. In a particular embodiment, the thrombin receptor binding domain or portion thereof comprises the amino acid sequence AGYKPDEGKRGDACEGDSGGPFV (i.e., amino acids 508-530 of human thrombin (SEQ ID NO:6)). In another embodiment, the thrombin receptor binding domain or portion thereof is a portion of the thrombin receptor binding domain and comprises the amino acid sequence EGKRGDACEG (SEQ ID NO:7).

As described herein, complementary peptides of domains of thrombin that are encoded by both the 5'-3' sequence of the antisense RNA strand and the 3'-5' sequence of the antisense RNA strand can be used to produce the NPAR agonist antibodies and antigen-binding domains of the invention. Therefore, in one embodiment, the complementary peptide (to which the antibodies and antigen-binding fragments bind) is encoded by the 5'-3' sequence of the antisense RNA strand. In another embodiment, the complementary peptide is encoded by the 3'-5' sequence of the antisense RNA strand.

In one example, a complementary peptide (to which the NPAR agonist antibodies and antigen-binding fragments of the invention bind) comprises the amino acid sequence KGSPTVTFTGIPCFPFIRLVTS (AC-23; SEQ ID NO:30). In another example, the complementary peptide comprises the amino acid sequence KGSPTVTFTGIPSFPFIRLVTS (23C53; SEQ ID NO:31). In yet another example, the complementary peptide comprises the amino acid sequence TFTGIPSFPF (C1053; SEQ ID NO:32). In still another example, the complementary peptide comprises the amino acid sequence RPMFGLLPFAPLRTLPLSPPGKQ [AC-23rev (SEQ ID NO:33), which is the complementary 5'-3' peptide corresponding to AC-23]. In still a further example, the complementary peptide comprises the amino acid sequence LPFAPLRTLP [C1053rev (SEQ ID NO:34), which is the complementary 5'-3' peptide corresponding to C1053].

One example of an NPAR agonist antibody or an antigen-binding fragment thereof binds to a cysteine-altering complementary peptide comprising the amino acid sequence KGSPTVTFTGIPSFPFIRLVTS (23C53; SEQ ID NO:31). 23C53, which differs from AC-23 by a single amino acid, is the complementary peptide of TP508, except that it possesses a single amino acid alteration from Cys to Ser.

In binding experiments using biotin-conjugated thrombin, thrombin was found to bind specifically to AC23 and 23C53. Half maximal binding of biotin-labeled thrombin to AC-23 was 4.8±0.2 nM (n=2±SD).

Addition of TP508 inhibited specific binding of biotin-labeled thrombin to AC-23. Up to 60% of the binding of thrombin to AC-23 can be inhibited by the addition of TP508. Therefore, both thrombin and TP508 bind to the complementary peptide, AC-23. This suggests that AC-23 has a three-dimensional structure that is similar to the thrombin-TP508 receptor on cells. Antibodies to AC-23 and other complementary peptides of thrombin can therefore be used to characterize the thrombin binding site that is activated by TP508, and can be used in the therapeutic and other methods described herein.

In addition to the thrombin receptor binding domain, the stimulatory (agonistic) thrombin polypeptide derivatives possess a domain (represented by amino acid residues 519-530 of human thrombin) with a high degree of homology to a number of serine esterases. However, the inhibitory (antagonistic) thrombin polypeptide derivatives do not include the serine esterase domain.

Thrombin peptide derivatives from amino acid residues 508-530 of human thrombin have been described for promoting thrombin receptor mediated cell stimulation. In addition, stimulatory (agonistic) thrombin polypeptide derivatives containing both fibronectin- and serine protease-homologous domains (residues 508 to 530 of human thrombin) bind to thrombin receptors with high-affinity and substitute for DIP-alpha-thrombin as an initiator of receptor occupancy-related mitogenic signals. (DIP-alpha-thrombin is a proteolytically inactive derivative of thrombin that retains receptor binding activity.) In contrast, inhibitory (antagonistic) thrombin polypeptide derivatives containing only the fibronectin-homologous domain (p517-520) (but not the serine protease-homologous domain) bind to the thrombin receptor without inducing mitogenesis. An intermediate thrombin peptide derivative (p519-530) retains the ability to mediate mitogenesis but to a much lesser degree than p508-530.

Molecular Recognition Theory

Blalock and Smith (1984) observed that the hydropathic character of an amino acid residue is related to the identity of the middle letter of the triplet codon from which it is transcribed (Blalock, J. E., and Smith, E. M., Biochem. Biophys. Res. Commun. 12: 203-07 (1984)). Specifically, a triplet codon with thymine (T) as its middle base codes for a hydrophobic residue while adenine (A) codes for a hydrophilic residue. A triplet codon with middle bases cytosine (C) or guanine (G) encode residues that are relatively neutral and with similar hydropathy scores. Hydropathy is an index of the affinity of an amino acid for a polar environment; hydrophilic residues yielding a more negative score, while hydrophobic residues exhibit more positive scores. Kyte and Doolittle (1982) conceived a hydropathy scale that is widely used (Kyte, J., and Doolittle, R. F., J. Mol. Biol. 5:105-32 (1982)). The observed relationship between the middle base of a triplet codon and residue hydropathy entails that peptides encoded by complementary DNA will exhibit complementary, or inverted, hydropathic profiles. It was proposed that because two peptide sequences encoded in complementary DNA strands display inverted hydropathic profiles, they may form amphipathic secondary structures, and bind to one another (Bost, K. L., et al., Proc. Natl. Acad. Sci. USA 82:1372-75 (1985)). Complementary peptides have been reported to form binding complexes with their "sense" peptide counterparts for a number of different systems (Root-Bernstein, R. S., and Holsworthy, D. D., J. Theor. Biol. 190:107-19 (1988)). For example, Gho and Chae describe peptide antagonists of human angiogenin that are complementary peptides encoded by the antisense RNA sequence corresponding to the receptor binding site of angiogenin (Gho, Y. S., and Chae, C. B. J. Biol. Chem. 272(39):24294-99 (1997)). Ghiso et al. describe a peptide complementary to a region of cystatin C that exhibits inhibitory activity (Ghiso, J., et al., Proc. Natl. Acad. Sci. USA 87(4):1288-91 (1990)), and Bost and Blalock describe the production of anti-idiotypic antibodies by immunization with a pair of complementary peptides (Bost. K. L., and Blalock, J. E., J. Molec. Recognit. 1:179-83 (1989)).

The scope of this analysis for explaining the interactions between proteins was further developed by Blalock to propose a Molecular Recognition Theory (MRT) (Bost, K. L., et al., Proc. Natl. Acad. Sci. USA 82:1372-75 (1985); Blalock, J. E., Nature Med. 1:876-78 (1995)). This theory suggests that a "molecular recognition" code of interaction exists between peptides that are encoded by complementary strands of DNA, based on the observation that such peptides will exhibit inverted hydropathic profiles. MRT has proved successful for predicting particular binding interactors.

Blalock suggested that it is the linear pattern of amino acid hydropathy scores in a sequence (rather than the combination of specific residue identities), that defines the secondary structure environment. Furthermore, he suggested that sequences with inverted hydropathic profiles are complementary in shape by virtue of inverse forces that determine their steric relationships.

Deriving a Complementary Peptide in the 3'-5' Reading Frame

As a corollary to his original work, Blalock contended that as well as reading a complementary codon in the usual 5'-3' direction, reading a complementary codon in the 3'-5' direction would also yield amino acid sequences that displayed opposite hydropathic profiles (Bost, K. L., et al., Proc. Natl. Acad. Sci. USA 82:1372-75 (1985)). This follows from the observation that the middle base of a triplet codon determines the hydropathy index of the residue it codes for, and therefore reading a codon in the reverse direction may change the identity, but not the hydropathic nature of the coded amino acid (Table 1).

TABLE 1

The relationships between amino acids and the residues encoded in the complementary strand
The relationships between amino acids and the residues encoded in the complementary strand reading 3'-5'

| Amino Acid | Codon | Complementary codon | Complementary Amino acid | Amino Acid | codon | Complementary codon | Complementary Amino acid |
|---|---|---|---|---|---|---|---|
| Alanine | GCA | CGU | Arginine | Serine | UCA | AGU | Serine |
| | GCG | CGC | | | UCC | AGQ | Arginine |
| | GCC | CGG | | | UCG | AGC | Serine |
| | GCU | CGA | | | UCU | AGA | Arginine |
| | | | | | AGC | UCG | Serine |
| | | | | | AGU | UCA | Serine |
| Arginine | CGG | GCC | Alanine | Glutamine | CAA | GUU | Valine |
| | CGA | GCU | Alanine | | CAG | GUC | Valine |
| | CGC | GCG | Alanine | | | | |
| | CGU | GCA | Alanine | | | | |
| | AGG | UCC | Serine | | | | |
| | AGA | UCU | Serine | | | | |
| Aspartic Acid | GAC | GUC | Valine | Glycine | GGA | CCU | Proline |
| | GAU | AUC | Isoleucine | | GGC | CCG | Proline |
| | | | | | GGU | CCA | Proline |
| | | | | | GGG | CCC | Proline |
| Asparagine | AAC | UUG | Leucine | Histidine | CAC | GUG | Valine |
| | AAU | UUA | Leucine | | CAU | GUA | Valine |
| Cysteine | UGU | ACA | Threonine | Isoleucine | AUA | UAU | Tyrosine |
| | UGC | ACG | Threonine | | AUC | UAG | Stop |
| | | | | | AUU | UAA | Stop |
| Glutamic Acid | GAA | CUU | Leucine | Leucine | CUG | GAC | Asp |
| | GAG | CUG | Leucine | | CUC | GAG | Glutamic acid |
| | | | | | CUU | GAA | Glutamic Acid |
| | | | | | UUA | AAU | Glutamic Acid |
| | | | | | CUA | GAU | Asparagine |
| | | | | | UUG | AAC | Aspartic Acid |
| | | | | | CUG | GAC | Asparagine Aspartic Acid |
| Lysine | AAA | UUU | Phenylalanine | Threonine | ACA | UGU | Cysteine |
| | AAG | UUC | Phenylalanine | | ACG | UGC | Cysteine |
| | | | | | ACC | UGG | Tryptophan |
| | | | | | ACU | UGA | Stop |

TABLE 1-continued

The relationships between amino acids and the residues
encoded in the complementary strand
The relationships between amino acids and the residues encoded in the complementary strand
reading 3'-5'

| Amino Acid | Codon | Complementary codon | Complementary Amino acid | Amino Acid | codon | Complementary codon | Complementary Amino acid |
|---|---|---|---|---|---|---|---|
| Methionine | AUG | UAC | Tyrosine | Tryptophan | UGG | ACC | Threonine |
| Phenylalanine | UUU | AAA | Lysine | Tyrosine | UAC | AUG | Methionine |
|  | UUC | AAG | Lysine |  | UAU | AUA | Isoleucine |
| Proline | CCA | GGU | Glycine | Valine | GUA | CAU | Histidine |
|  | CCC | GGG | Glycine |  | GUG | CAC | Histidine |
|  | CCU | GGA | Glycine |  | GUC | CAG | Glutamine |
|  | CCG | GGC | Glycine |  | GUU | CAA | Glutamine |

Antibodies and Antibody Producing Cells

NPAR agonists as referred to herein encompass antibodies and antigen-binding fragments thereof that bind to the complementary peptides described herein and activate the non-proteolytically activated thrombin receptor. The antibodies as referred to herein can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. In one embodiment, the antibody or antigen-binding fragment is a monoclonal antibody or antigen-binding fragment thereof. The term "monoclonal antibody" or "monoclonal antibody composition" as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

The term "antibody" as used herein also encompasses functional fragments of antibodies, including fragments of chimeric, humanized, primatized, veneered or single chain antibodies. Functional fragments include antigen-binding fragments of antibodies that bind to the complementary peptides, wherein complementary peptides are encoded by the complement of a nucleotide sequence encoding thrombin or a portion thereof. For example, antibody fragments capable of binding to a complementary peptide, include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the $CH_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, are also encompassed by the term antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213).

The antibody can be a humanized antibody comprising one or more immunoglobulin chains [e.g., an antibody comprising a complementarity-determining region (CDR) of nonhuman origin (e.g., one or more CDRs derived from an antibody of nonhuman origin)] and a framework region derived from a light and/or heavy chain of human origin (e.g., CDR-grafted antibodies with or without framework changes)]. In one embodiment, the antibody or antigen-binding fragment thereof comprises the light chain CDRs (CDR1, CDR2 and CDR3) and heavy chain CDRs (CDR1, CDR2 and CDR3) of a particular immunoglobulin. In another embodiment, the antibody or antigen-binding fragment further comprises a human framework region.

Antibodies that are specific for a complementary peptide, wherein the complementary peptide is encoded by the complement of a nucleotide sequence encoding thrombin or a portion thereof, can be raised against an appropriate immunogen, such as a synthetic or recombinant complementary peptide or a portion thereof. Antibodies can also be raised by immunizing a suitable host (e.g., mouse) with transfected cells that express a complementary peptide. Such cells can also be used in a screen for an antibody that binds thereto (See e.g., Chuntharapai et al., J. Immunol., 152: 1783-1789 (1994); Chuntharapai et al., U.S. Pat. No. 5,440,021).

Preparation of Immunizing Antigen, and Polyclonal and Monoclonal Antibody production can be performed using any suitable technique (e.g., as exemplified herein). A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line, such as SP2/0, P3X63Ag8.653 or a heteromyeloma) with antibody-producing cells. Antibody-producing cells can be obtained from the peripheral blood or, preferably the spleen or lymph nodes, of humans or other suitable animals immunized with a complementary peptide. The fused cells (hybridomas) can be isolated using selective culture conditions, and cloned by limiting dilution. Cells that produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods that select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., Proc. Natl. Acad. Sci. USA, 90: 2551-2555 (1993); Jakobovits et al., Nature, 362: 255-258 (1993)). Additional methods that are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO 97/13852).

The invention also encompasses bispecific antibodies, or functional fragments thereof (e.g., F(ab')$_2$), which bind to a complementary peptide as described herein and at least one other antigen (e.g., a tumor antigen, a viral antigen). Bispecific antibodies can be secreted by triomas and hybrid hybridomas. Generally, triomas are formed by fusion of a hybridoma and a lymphocyte (e.g., antibody-secreting B cell) and hybrid hybridomas are formed by fusion of two hybridomas. Each of the fused cells (i.e., hybridomas, lymphocytes) produces a monospecific antibody. However, triomas and hybrid hybridomas can produce an antibody containing antigen-binding sites that recognize different antigens. The supernatants of triomas and hybrid hybridomas can be assayed for bispecific antibody using a suitable assay (e.g., ELISA), and bispecific antibodies can be purified using conventional methods. (see, e.g., U.S. Pat. No. 5,959,084 (Ring et al.), U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

Angiogenic Growth Factors

An "angiogenic growth factor" is a polypeptide which stimulates the development of blood vessels, e.g., promotes angiogenesis, endothelial cell growth, stability of blood vessels, and/or vasculogenesis. For example, angiogenic factors, include, but are not limited to, e.g., VEGF and members of the VEGF family, P1GF, PDGF family, fibroblast growth factor family (FGFs), TIE ligands (Angiopoietins), ephrins, ANGPTL3, ANGPTL4, etc. Angiogenic factors also include polypeptides such as growth hormone, insulin-like growth factor-I (IGF-I), VIGF, epidermal growth factor (EGF), CTGF and members of its family, and TGF-α and TGF-β. See, e.g., Klagsbrun and D'Amore, Annu. Rev. Physiol., 53:217-39 (1991); Streit and Detmar, Oncogene, 22:3172-3179 (2003); Ferrara & Alitalo, Nature Medicine 5(12):1359-1364 (1999); Tonini et al., Oncogene, 22:6549-6556 (2003); and, Sato Int. J. Clin. Oncol., 8:200-206 (2003).

The term "VEGF" (also referred to as "VEGF-A") as used herein refers to vascular endothelial cell growth factor protein A. The term "human VEGF" (also referred to as "human VEGF-A") as used herein refers to any of the isoforms of human vascular endothelial cell growth factor. Described isoforms (arising by differential mRNA splicing) include 121, 145, 148, 165, 165b, 183, 189 and 206. See, for example, Table 2 and Leung et al., Science 246:1306 (1989), and Houck et al., Mol. Endocrin. 5:1806 (1991). "Human VEGF" also includes naturally occurring allelic variants of human VEGF-A and variants arising by variations in post-translational modifications. Table 2 is not intended to be comprehensive or limiting. Angiogenic growth factors in Table 2 are human unless otherwise indicated.

TABLE 2

Examples of Angiogenic Growth Factors of VEGF Family

| Angiogenic Growth Factor | Receptor | Chromosome Location | GenBank No. | Reference |
|---|---|---|---|---|
| Human VEGF-A | VEGFR1 VEGFR2 | 6p12 | NM_003376 | |
| isoforms: 121 | | | | |
| 145 | | | | |
| 148 | | | | |
| 165 | | | | |
| 165b | | | | |
| 183 | | | | |
| 189 | | | | |
| 206 | | | | |
| Human VEGF-B | VEGFR1 | 11q13 | NM_003377 | |
| Human VEGF-C | VEGFR3 VEGFR2 | 4q34.1-q34.3 | NM_005429 | |
| Human VEGF-D | VEGFR3 VEGFR2 | Xp22.31 | NM_004469 | |
| VEGF-E [Orf virus (D1701)] | VEGFR2 | | AF106020 | |
| VEGF-E [Orf virus (NZ2)] | VEGFR2 | | S67520 | |
| VEGF-E [Orf virus (NZ7)] | VEGFR2 | | S67522 | |
| VEGF-E$_{N27}$/PlGF (chimeric) | VEGFR2 | | | 1, 2 |
| VEGF-E/PlGF (chimeric) | VEGFR2 | | | 3 |
| PlGF | FLT1 VEGFR1 | 14q22-q24.3 | NM_002632 | |
| isoforms: PlGF1 | | | | |
| PlGF2 | | | | |
| PlGF3 | | | | |
| PlGF4 | | | | |
| VEGF-F (viper) | VEGFR2 | | | 4 |
| D. melanogaster PV1 | | | NM_078683 | 5 |
| D. melanogaster PVF2 | | | NM_078775 | 5 |
| D. melanogaster PVF3 | | | NM_078776 | 5 |

References
1. Zheng, Y. et al., "Chimeric VEGF-ENZ7/PlGF Promotes Angiogenesis Via VEGFR-2 Without Significant Enhancement of Vascular Permeability and Inflammation," Arterioscler. Throm. Vasc. Biol. 26: 2019-2026 (2006).
2. Zheng, Y. et al., "Chimeric VEGF-ENZ7/PlGF Specifically Binding to VEGFR-2 Accelerates Skin Wound Healing via Enhancement of Neovascularization," Arterioscler. Throm. Vasc. Biol. 27: 503-511 (2007).
3. Inoue, N. et al., "Therapeutic Angiogenesis Using Novel Vascular Endothelial Growth Factor-E/Human Placental Growth Factor Chimera Genes," Arterioscler. Throm. Vasc. Biol. 27: 99-105 (2007).
4. Suto, K. et al., "Crystal structures of novel vascular endothelial growth factors (VEGF) from snake venoms: insight into selective VEGF binding to kinase insert domain-containing receptor but not to fms-like tyrosine kinase-1," J. Biol. Chem 280(3): 2126-2131 (2005).
5. Duchek, P., "Guidance of cell migration by the *Drosophila* PGDF/VEGF receptor," Cell 107(1): 17-26 (2001).

Human VEGF-A exists as a number of isoforms that arise from alternative splicing of mRNA of a single gene organized into 8 exons located on chromosome 6 (see, e.g., Ferrara N, Davis Smyth T. Endocr Rev 18:1-22 (1997); and, Henry and Abraham, Review of Preclinical and Clinical Results with Vascular Endothelial Growth Factors for Therapeutic Angiogenesis, Current Interventional Cardiology Reports, 2:228-241 (2000)). See also, U.S. Pat. Nos. 5,332,671 and 6,899,882. In one embodiment, $VEGF_{165}$ is administered in the methods of the invention (e.g., recombinant human $VEGF_{165}$). $VEGF_{165}$, the most abundant isoform, is a basic, heparin binding, dimeric covalent glycoprotein with a molecular mass of about 45,000 Daltons (Id). $VEGF_{165}$ homodimer consists of two 165 amino acid chains. The protein has two distinct domains: a receptor binding domain (residues 1-110) and a heparin binding domain (residues 110-165). The domains are stabilized by seven intramolecular disulfide bonds, and the monomers are linked by two interchain disulfide bonds to form the native homodimer. $VEGF_{121}$ lacks the heparin binding domain (see, e.g., U.S. Pat. No. 5,194,596), whereas $VEGF_{189}$ (see, e.g., U.S. Pat. Nos. 5,008,196; 5,036,003; and 5,240,848) and $VEGF_{206}$ are sequestered in the extracellular matrix.

The term "angiogenic growth factor" also includes those below in Table 3. The list in Table 3 is not intended to be comprehensive or limiting.

TABLE 3

Examples of Other Angiogenic Growth Factors

Angiogenin
Angiopoietin-1
Del-1
Acidic fibroblast growth factor (aFGF or FGF-1[1,2])
Basic fibroblast growth factor (bFGF or FGF-2[3,4])
Fibroblast growth factor 4 (FGF 4)
Follistatin
Granulocyte colony-stimulating factor (G-CSF)
Hepatocyte growth factor (HGF)/scatter factor (SF)
Interleukin-8 (IL-8)
Leptin
Midkine
Platelet-derived endothelial cell growth factor (PD-ECGF)
Platelet-derived growth factor-BB (PDGF-BB) (rhPDGF-BB is Regranex ®)
Pleiotrophin (PTN)
Progranulin
Proliferin
Transforming growth factor-alpha (TGF-alpha)
Transforming growth factor-beta (TGF-beta)
Tumor necrosis factor-alpha (TNF-alpha)
Vascular endothelial growth factor (VEGF)/vascular permeability factor (VPF)
Thymosin beta 4 (Tβ4)
Connective tissue growth factor
Osteopontin
Insulin growth factor (IGF-1)

| Angiogenic Growth Factor | Receptor | Chromosome Location | GenBank No. | Reference |
|---|---|---|---|---|
| PDGFD | PDGFR-α PDGFR-β | 11q22.3 | NM_025208 | |
| PDGF-α | | 7p22 | NM_002607 | |
| PDGF2 | | 22q12.3-q13.1 | NM_002608 | |
| PDGFC | PDGF-α | 4q32 | NM_016205 | | isoforms:
1 (241 amino acids)
2 (226 amino acids)

References
[1]Schumacher, B., et al., "Induction of neoangeogenesis in ischemic myocardium by human growth factors: first clinical results of a new treatment of coronary heart disease," Circulation 97: 645-650 (1998).
[2]Stegmann, T. J. et al., "Induction of myocardial neoangiogenesis by human growth factors: a new therapeutic option in coronary heart disease," Herz 25: 589-599 (2000).
[3]Selke, F. W., et al., "Therapeutic angiogenesis with basic fibroblast growth factor: technique and early results," Ann. Thorac. Surg. 65: 1540-1544 (1998).
[4]Laham, R. J., et al., "Local perivascular delivery of basic fibroblast growth factor in patients undergoing coronary bypass surgery: results of a phase 1 randomized, double-blind, placebo-controlled trial, "Circulation 100: 1865-1871 (1999).

A "native" polypeptide (e.g., a native angiogenic factor) is a polypeptide having the same amino acid sequence as a polypeptide isolated from a natural source. Thus, a native polypeptide can have the amino acid sequence of naturally occurring polypeptide from any mammal, e.g., a human. Such native polypeptides can be isolated from nature or can be produced by recombinant or synthetic means. The term native polypeptide encompasses naturally occurring truncated or secreted forms of the polypeptide (e.g., an extracellular domain sequence), allelic forms designated as wild type, naturally occurring variant forms (e.g., alternatively spliced iso forms) and naturally occurring allelic variants of the polypeptide.

A "polypeptide variant" (e.g., a polypeptide variant of an angiogenic factor) means a biologically active polypeptide having at least about 80% amino acid sequence identity with the native polypeptide. Such "polypeptide variants" include, for instance, polypeptides wherein one or more amino acid residues are added, or deleted, at the N- and/or C-terminus of the polypeptide relative to a native polypeptide. Ordinarily, a polypeptide variant will have at least about 80% amino acid sequence identity, or at least about 90% amino acid sequence identity, or at least about 95% or more amino acid sequence identity with the native polypeptide. Polypeptide variants include polypeptides that comprise one or more amino acid substitutions, additions or deletions, or combinations of any of these differences from the native polypeptide. Polypeptide variants can have, for instance, several, such as 5 to 10, 1 to 5, or 4, 3, 2 or 1 amino acids substituted, deleted, or added, in any combination, compared to native polypeptides. In one embodiment, variants have silent substitutions, additions and/or deletions that do not significantly alter the properties and activities of the polypeptide compared to the native polypeptide. Polypeptide variants can also be modified polypeptides in which one or more amino acid residues are modified. Polypeptide variants can be prepared by a variety of methods well known in the art. Polypeptide variants differing by amino acid sequence from a native polypeptide can be prepared by mutations in the encoding DNA. Polypeptide variants also include polypeptides that differ from native polypeptides in glycosylation or other post-translational modification.

A polypeptide variant can be prepared, for instance, by site-directed mutagenesis of nucleotides in the DNA encoding the native polypeptide or by phage display techniques, thereby producing DNA encoding the variant, and thereafter expressing the DNA in recombinant cell culture.

Amino acid deletions generally range from about 1 to 30 residues, optionally 1 to 10 residues, optionally 1 to 5 or less, and typically are contiguous.

Amino acid sequence additions include amino- and/or carboxyl-terminal fusions of from one residue to polypeptides of essentially unrestricted length as well as intrasequence insertions of single or multiple amino acid residues. Intrasequence additions (i.e., additions within a native polypeptide sequence) may range generally from about 1 to 10 residues, optionally 1 to 5, or optionally 1 to 3. An example of a terminal insertion includes a fusion of a signal sequence, whether heterologous or homologous to the host cell, to the N-terminus to facilitate the secretion from recombinant hosts.

Additional polypeptide variants are those in which at least one amino acid residue in the native polypeptide has been removed and a different amino acid residue inserted in its place (substitution). Conservative substitutions in polypeptide variants of an angiogenic growth factor may be made in accordance with those shown in Table 4, wherein both exemplary and preferred substitutions are conservative substitutions in polypeptide variants of an angiogenic growth factor. Polypeptide variants can also comprise unnatural amino acids as described herein.

Amino acids may be grouped according to similarities in the properties of their side chains (A. L. Lehninger, Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring amino acids may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

TABLE 4

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

"Naturally occurring amino acid residues" (i.e. amino acid residues encoded by the genetic code) may be selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). A "non-naturally occurring amino acid residue" refers to an amino acid residue, other than those naturally occurring amino acid residues listed above, which can be bound to adjacent amino acid residues(s) in a polypeptide chain through peptide bonds. Examples of non-naturally occurring amino acid residues include, e.g., norleucine, ornithine, norvaline, homoserine and other amino acid residue analogues such as those described in Ellman et al. Meth. Enzym. 202: 301-336 (1991) and US Patent application publications 20030108885 and 20030082575.

"Percent (%) amino acid sequence identity" herein is defined as the percentage of amino acid residues in a candidate sequence of an angiogenic growth factor that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Portions of an angiogenic growth factor include polypeptides that are shorter than a corresponding native polypeptide, and comprise at least 20 contiguous amino acid residues of the corresponding native polypeptide, that share 75% to 100% amino-acid sequence identity with the native polypeptide. In particular embodiments, the portion shares at least 90% or 95% amino acid sequence identity with the native polypeptide. Portions of an angiogenic growth factor can be synthesized, and can have an N-terminal amino group and a C-terminal carboxyl group as they occur in proteins isolated from natural sources, or can have a modified N-terminus (e.g., acylated) and/or a modified C-terminus (e.g., amidated). Portions of an angiogenic growth factor can be generated through the expression of genes constructed for the purpose of producing the portion. Portions may be cyclic or linear. In all cases, portions of an angiogenic growth factor have at least 50% of the biological activity of the corresponding native polypeptide, as measured by an assay appropriate to measuring the angiogenic activity of the corresponding native polypeptide.

A number of assays have been used previously to measure angiogenic activity and have been described. An angiogenic growth factor, whether it is a native polypeptide, polypeptide variant, portion of an angiogenic growth factor, or fusion protein of an angiogenic growth factor, can be tested by an in vitro or in vivo assay to assess its activity, using one or more of the assays described herein, or other suitable assay such as those known to persons of ordinary skill in the art. Not all assays are appropriate to measure the angiogenic activity of a given angiogenic growth factor.

A rabbit corneal assay has been described, in which angiogenic growth factor implanted into cornea stimulates the growth of new capillaries. See Ziche et al., Lab. Invest. 61:629-634 (1989). An in vitro angiogenesis assay system allows for observation of morphological changes in endothelial cells stimulated by angiogenic growth factor. See Montesano et al., J. Cell Biol. 97:1648-1652 (1983). Angiogenic growth activity can also be measured by an assay for cell growth [Marconcini et al., Proc. Natl. Acad. Sci. USA 96: 9671-9676 (1999)] in response to the angiogenic growth factor, or by chemotaxis assays as described in Examples 6 and 7.

A fusion protein of an angiogenic growth factor comprises a biologically active native polypeptide or biologically active portion thereof (as described above) as a first moiety, linked to second moiety not occurring in the native polypeptide. Thus, the second moiety can be an amino acid or polypeptide. The first moiety can be in an N-terminal location, C-terminal location or internal to the fusion protein. In one embodiment, the fusion protein comprises a biologically active polypeptide that consists of the amino acid sequence of a naturally occurring angiogenic growth factor or biologically active portion thereof as the first moiety, and a second moiety comprising a linker sequence and an affinity ligand.

A fusion protein of an angiogenic growth factor can be produced by a variety of methods. For example, a fusion protein can be produced by the insertion of gene encoding an angiogenic growth factor or portion thereof into a suitable expression vector. The resulting construct can be introduced into a suitable host cell for expression. Upon expression, fusion protein can be purified from a cell lysate by means of a suitable affinity matrix, for example (see e.g., *Current Protocols in Molecular Biology*. Ausubel, F. M. et al., eds., pp. 16.4.1-16.7.8, containing supplements up through Supplement 28, 1994). See, for examples of VEGF fusion (chimeric) proteins, Zheng, et al., Arterioscler. Thromb. Vas. Biol. 2006; 26: 2019-2026 and Inoue, et al., Arterioscler. Thromb. Vasc. Biol. 2007; 27: 99-105.

Angiogenic growth factors can be of human origin or of non-human (preferably mammalian) origin. Human angiogenic growth factors as well as non-human species homologs are angiogenic growth factors and can be used in the combination therapies of the invention. A homolog preferably has at least 70% amino acid sequence identity, more preferably, at least 80% sequence identity and, even more preferably, at least 90% sequence identity with a human angiogenic growth factor.

In accordance with the present invention, "angiogenic growth factors" encompass native angiogenic growth factors, portions of angiogenic growth factors, polypeptide variants of angiogenic growth factors and fusion proteins of angiogenic growth factors as described above.

Methods of Treatment with NPAR Agonists

The present invention is directed to methods of treating endothelial dysfunction at a site in a subject in need thereof comprising administering vascularly to the subject a therapeutically effective amount of an NPAR agonist, wherein the site is not an artery injured by angioplasty, a chronic skin ulcer, a site in need of osteoinduction or a site in need of cardiac revascularization. The subject may suffer from one or more of a variety of diseases or conditions that will benefit from reversing or inhibiting endothelial dysfunction. Such diseases or conditions may include, but are not limited to, hypertension, congestive heart failure, coronary artery disease, stroke, cerebrovascular disease, peripheral vascular disease, diabetes, erectile dysfunction, atherosclerosis, asthma, rheumatoid arthritis, pulmonary hypertension, acute lung injury, chronic obstructive pulmonary disease (COPD), cystic fibrosis, inflammatory lung disease, hyperhomocysteinemia, sickle cell disease, pre-eclampsia, chronic renal failure, chronic renal dysfunction, renal microvascular disease, hepatic reperfusion injury, neuropathy, Alzheimer's disease, thyroid disease, sepsis, thrombosis, multiple organ failure, inflammatory bowel disease, and radiation damage. In a specific embodiment, the disease is hypertension. In another specific embodiment, the disease is atherosclerosis. In yet another specific embodiment, the disease is peripheral vascular disease. In still another specific embodiment, the disease is asthma.

A "subject" is preferably a human, but can also be an animal in need of treatment with a NPAR agonist disclosed herein, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a NPAR agonist, are subjects with diseases and/or conditions that can be treated with NPAR agonists to achieve a beneficial therapeutic and/or prophylactic result. A beneficial outcome includes a decrease in the severity of symptoms or delay in the onset of symptoms, increased longevity and/or more rapid or more complete resolution of the disease or condition.

An "effective amount" is the quantity of the NPAR agonist that results in an improved clinical outcome of the condition being treated with the NPAR agonist compared with the absence of treatment. The amount of the NPAR agonist administered will depend on the degree, severity, and type of the disease or condition, the amount of therapy desired, and the release characteristics of the pharmaceutical formulation. It will also depend on the subject's health, size, weight, age, sex and tolerance to drugs. Typically, the agonist is administered for a sufficient period of time to achieve the desired therapeutic effect. Typically, from about 1 µg per day to about 1 mg per day of the NPAR agonist (preferably from about 5 µg per day to about 100 µg per day) is administered to the subject in need of treatment, especially for a local means of administration. The NPAR agonist can also be administered at a dose of from about 0.1 mg/kg/day to about 10 mg/kg/day, with from about 0.2 mg/kg/day to about 1 mg/kg/day being preferred, especially for systemic means of administration. Typical dosages for the NPAR agonists of the invention are also 5-500 mg/day, preferably 25-250 mg/day, especially for systemic means of administration. For methods in which a combination of NPAR agonist and angiogenic growth factor are administered to a subject, the angiogenic growth factor (e.g., VEGF-A) can be administered in a dosage which can be determined by one of ordinary skill in the art, according to the nature of the disease or disorder, the site of treatment, the age, gender, weight and other conditions of the subject. Appropriate dosages of angiogenic growth factor are 1 µg/kg to 50 mg/kg (e.g., 0.1-20 mg/kg).

"Treating" means that following a period of administering the NPAR agonist or composition comprising an NPAR agonist, a beneficial therapeutic and/or prophylactic result is achieved, which can include a decrease in the severity of symptoms or delay in or inhibition of the onset of symptoms, increased longevity and/or more rapid or more complete resolution of the disease or condition, or other improved clinical outcome as measured according to the site that is being observed or the parameters measured for a particular disease or disorder. "Treating" also includes inhibiting or delaying the onset of a disease, disorder or medical condition, and can also mean decreasing the probability of developing such disease, disorder or medical condition, in a subject, wherein the subject is, for example, a subject who is at risk for developing the disease, disorder or condition.

The disclosed NPAR agonists can be administered by any suitable route, locally (e.g., topically) or systemically, including, for example, by parenteral administration. Parenteral administration can include, for example, intramuscular, intravenous, subcutaneous, or intraperitoneal injection or vascular administration, and can also include transdermal patch and implanted slow-release devices such as pumps. Topical administration can include, for example, creams, gels, ointments or aerosols. Respiratory administration can include, for example, inhalation or intranasal drops. For certain indications, it is advantageous to inject or implant an NPAR agonist directly to the treatment site. The NPAR agonist can be advantageously administered in a sustained release formulation. The NPAR agonist can be administered chronically, wherein the agonist is administered over a long period of time (at least 60 days, but more typically, for at least one year), at intervals or by a continuous delivery method, to treat a chronic or recurring disease or condition.

Administration of a combination comprising therapeutic agents includes simultaneous (concurrent) administration as well as consecutive administration in any order over a period of treatment time. The agents can be administered together in one composition or can be administered in separate compositions. The NPAR agonist can be administered through the same administration route as the angiogenic growth factor. The NPAR agonist can also be administered through a different administration route from that of the angiogenic growth factor. The NPAR agonist and the angiogenic growth factor can have the same or different administration schedules.

The NPAR agonists can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site. Examples of pharmaceutically acceptable carriers include, for example, saline, aerosols, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

The compositions used in the present invention to treat endothelial dysfunction can additionally comprise a pharmaceutical carrier in which the thrombin peptide derivative or NPAR agonist is dissolved or suspended. Examples of pharmaceutically acceptable carriers include, for example, saline, aerosols, commercially available inert gels, or liquids supplemented with albumin, methyl cellulose or a collagen matrix. Typical of such formulations are gels. Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent or can be mixed after the gelation process.

In one embodiment, the NPAR agonists are administered in a sustained release formulation. Polymers are often used to form sustained release formulations. Examples of these polymers include poly α-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28:5 (1997), the entire teachings of which are incorporated herein by reference). The incorporation of poly(ethylene glycol) into the polymer as a blend to form microparticle carriers allows further alteration of the release profile of the active ingredient (see Cleek et al., *J. Control Release* 48:259 (1997), the entire teachings of which are incorporated herein by reference). Ceramics such as calcium phosphate and hydroxyapatite can also be incorporated into the formulation to improve mechanical qualities.

PPHOS polymers contain alternating nitrogen and phosphorous with no carbon in the polymer backbone, as shown below in Structural Formula (II):

(II)

The properties of the polymer can be adjusted by suitable variation of side groups R and R' that are bonded to the polymer backbone. For example, the degradation of and drug release by PPHOS can be controlled by varying the amount of hydrolytically unstable side groups. With greater incorporation of either imidazolyl or ethylglycol substituted PPHOS, for example, an increase in degradation rate is observed (see Laurencin et al., *J Biomed Mater. Res.* 27:963 (1993), the entire teachings of which are incorporated herein by reference), thereby increasing the rate of drug release.

Polyanhydrides, shown in Structural Formula (III), have well defined degradation and release characteristics that can be controlled by including varying amounts of hydrophobic or hydrophilic monomers such as sebacic acid and 1,3-bis(p-carboxyphenoxy)propane (see Leong et al., *J. Biomed. Mater. Res.* 19:941 (1985), the entire teachings of which are incorporated herein by reference). To improve mechanical strength, anhydrides are often copolymerized with imides to form polyanhydride-co-imides. Examples of polyanhydride-co-imides that are suitable for orthopaedic applications are poly(trimellitylimido-glycine-co-1,6-bis(carboxyphenoxy)hexane and pyromellityimidoalanine: 1,6-bis(p-carboxyphenoxy)hexane copolymers.

(III)

Injectable delivery formulations may be administered intravenously or directly at the site in need of treatment. The injectable carrier may be a viscous solution or gel.

Delivery formulations include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. Injectable matrices include polymers of poly(ethylene oxide) and copolymers of ethylene and propylene oxide (see Cao et al., *J. Biomater. Sci* 9:475 (1998) and Sims et al., *Plast Reconstr. Surg.* 98.843 (1996), the entire teachings of which are incorporated herein by reference).

Methods for encapsulating compositions (such as in a coating of hard gelatin or cyclodextran) are known in the art (Baker, et al., "Controlled Release of Biological Active Agents", John Wiley and Sons, 1986).

Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration.

Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration.

Gels contain a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

Diseases and conditions that are treatable with the disclosed NPAR agonists are often accompanied by symptoms and infirmities such as pain and infection. In certain instances it may be advantageous to co-administer one or more additional pharmacologically active agents along with an NPAR agonist to address such issues. For example, managing pain and inflammation may require co-administration with analgesic or an anti-inflammatory agents. Managing infection may require co-administration with antimicrobial, antibiotic or disinfectant agents.

An NPAR agonist can be administered to a subject alone or in combination with one or more other therapeutics, for example, a cholesterol-lowering agent, an anti-hypertensive agent, a beta-blocker, an anti-coagulent, a thrombolytic agent, an analgesic, an anti-inflammatory agent, an anti-plaque agent, insulin, a nitric oxide generating agent, an antiviral agent or an antibiotic. In one method, an NPAR agonist can be administered to a subject in combination with arginine, for example, with arginine as an oral nutritional supplement.

Thrombin peptide derivatives and modified thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48-267; and Barany and Merrifield, in *The Peptides*, E. Gross and J. Meienhofer, Eds., Academic Press, New York, 1980, pp. 3-285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these six articles are incorporated herein by reference in their entirety.

Thrombin peptide derivative dimers can be prepared by oxidation of the monomer. Thrombin peptide derivative dimers can be prepared by reacting the thrombin peptide derivative with an excess of oxidizing agent. A well-known suitable oxidizing agent is iodine.

A "non-aromatic heterocyclic group" as used herein, is a non-aromatic carbocyclic ring system that has 3 to 10 atoms and includes at least one heteroatom, such as nitrogen, oxygen, or sulfur. Examples of non-aromatic heterocyclic groups include piperazinyl, piperidinyl, pyrrolidinyl, morpholinyl, thiomorpholinyl.

The term "aryl group" includes both carbocyclic and heterocyclic aromatic ring systems. Examples of aryl groups include phenyl, indolyl, furanyl and imidazolyl.

An "aliphatic group" is a straight chain, branched or cyclic non-aromatic hydrocarbon. An aliphatic group can be completely saturated or contain one or more units of unsaturation (e.g., double and/or triple bonds), but is preferably saturated, i.e., an alkyl group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. Aliphatic groups include, for example, methyl, ethyl, n-propyl, iso-propyl, n-butyl, sec-butyl, tert-butyl, pentyl, cyclopentyl, hexyl, cyclohexyl, octyl and cyclooctyl.

Suitable substituents for an aliphatic group, an aryl group or a non-aromatic heterocyclic group are those which do not significantly lower therapeutic activity of the NPAR agonist, for example, those found on naturally occurring amino acids. Examples include —OH, a halogen (—Br, —Cl, —I and —F), —O($R_e$), —O—CO—($R_e$), —CN, —$NO_2$, —COOH, =O, —$NH_2$—NH($R_e$), —N($R_e$)$_2$, —COO($R_e$), —$CONH_2$, —CONH($R_e$), —CON(W)$_2$, —SH, —S($R_e$), an aliphatic group, an aryl group and a non-aromatic heterocyclic group. Each $R_e$ is independently an alkyl group or an aryl group. A substituted aliphatic group can have more than one substituent.

The invention is illustrated by the following examples which are not intended to be limiting in any way.

Example 1

Materials and Methods

Endothelial Cell Culture

Human coronary artery endothelial cells (HCAE cells, Cambrex Bio Science Walkersville, Walkersville, Md.) were cultured in 5% CO2 at 37° C. in endothelial cell growth medium (EGM) supplemented with 2% fetal bovine serum and Single Quot supplements (Clonetics, San Diego, Calif.; containing epidermal growth factor, hydrocortisone, vascular endothelial growth factor, fibroblast growth factor, insulin growth factor, ascorbic acid, heparin, gentamycin, and amphotericin B). Cells were used between passages 4 and 6 for these studies. HCAE cells were plated at a density of 50,000 cells per well in 12-well plates and were grown for 3 days to reach confluency. Two-day post-confluent cells were treated with TNFα or TP508. Cells were then incubated in normoxic or 1% hypoxic conditions for the indicated times. In some experiments, cells were pretreated with TP508 for 1 h before TNFα stimulation. For RNA extraction, HCAE cells were cultured in 6-well plates.

RT-PCR

Total RNA was isolated using an Ambion isolation kit as described by the manufacturer.

RT-PCR for eNOS was performed by Ready-to-Go RT-PCR Beads (Amersham Biosciences) using a two-step protocol. First, cDNA synthesis was achieved by incubating 1 µg total RNA with 1 µg random hexamers (pdN6) as primers and M.-MuLV reverse transcriptase at 42° C. for 60 min. Then, after heating at 95° C. for 5 min, PCR was carried out performing 25 or 30 cycles of denaturation (95° C. for 30 s), annealing (62° C. for 30 s), and extension (72° C. for 30 s), ending with a single final extension at 72° C. for 7 min. The sequences for human eNOS primers were as follows: sense 5'-GCA CCG GCA TCA CCA GGA AGA AGA-3' (SEQ ID NO:35) and antisense 5'-CCG CCG CCA AGA GGA CAC CAG T-3' (SEQ ID NO:36) (Sitges, M. et al., Int. J. Cardiol. 105(1):74-79, 2005). 18S primers (Ambion) were used to amplify 18S ribosomal RNA as an internal normalization control. PCR-amplified products were visualized by 1% agarose gel electrophoresis.

SYBR Green Real-Time PCR

Real time quantitative PCR was used to determine relative expression of eNOS mRNA in endothelial cells treated with TP508 or TNF. Samples were coded to provide blinded analysis. One µg of total RNA was reverse-transcribed using Taqman Reverse Transcription Reagents Kit (ABI) as specified by the manufacturer. Quantitative PCR amplifications were done using 2 µl of cDNA in a total volume of 25 µl using SYBR green probes in the SYBR Green PCR Master Mix (ABI). All PCR assays were run in the ABI Prism 7000 Sequence Detection System. The SYBR green PCR primers were as follows: human eNOS sense: 5'-GCG GCT GCA TGA CAT TGA G-3' (SEQ ID NO:37), antisense: 5'-GTC GCG GTA GAG ATG GTC AAG T-3' (SEQ ID NO:38). The reverse-transcribed cDNA sample cycle threshold values were determined from triplicate samples and normalized to the 18S "housekeeping" gene.

Western Blot Analysis

The cell lysates were subjected to SDS-PAGE in a 10% polyacrylamide gel and transferred to a nitrocellulose membrane (0.2-µm, Invitrogen). After blocking with 5% milk, the membrane was incubated overnight at 4° C. with primary antibodies against phospho-eNOS (Ser 1177) and eNOS (Cell Signaling Technology, Beverly, Mass.), human type-1 arginase (clone 9C5) (Cell Sciences, Canton, Mass.), or GAPDH (Santa Cruz Biotechnology, Santa Cruz, Calif.). HRP-conjugated anti-mouse or anti-rabbit antibodies (Cell Signaling Technology) were used as secondary antibodies (HRP, horseradish peroxidase). The immunoblots were developed using Immobilon Western Detection Reagents (Millipore Corporation).

Example 2

TP508 Blocks TNFα Induced Upregulation of Arginase 1

As described above, ED and loss of NO dependent signaling can arise either from a decrease in NOS activity or by an increase in arginase activity that depletes cellular levels of L-arginine. In both hypoxia and inflammation, it has been reported that the level of TNFα is elevated and is thought to contribute to ED by affecting one or both of these NO related activities. To evaluate the potential effects of TP508 on ED, we cultured early passage human coronary artery endothelial cells (HCAE cells) under normoxic conditions and treated them with TNFα alone or with the combination of TNFα and TP508.

Figure 2:
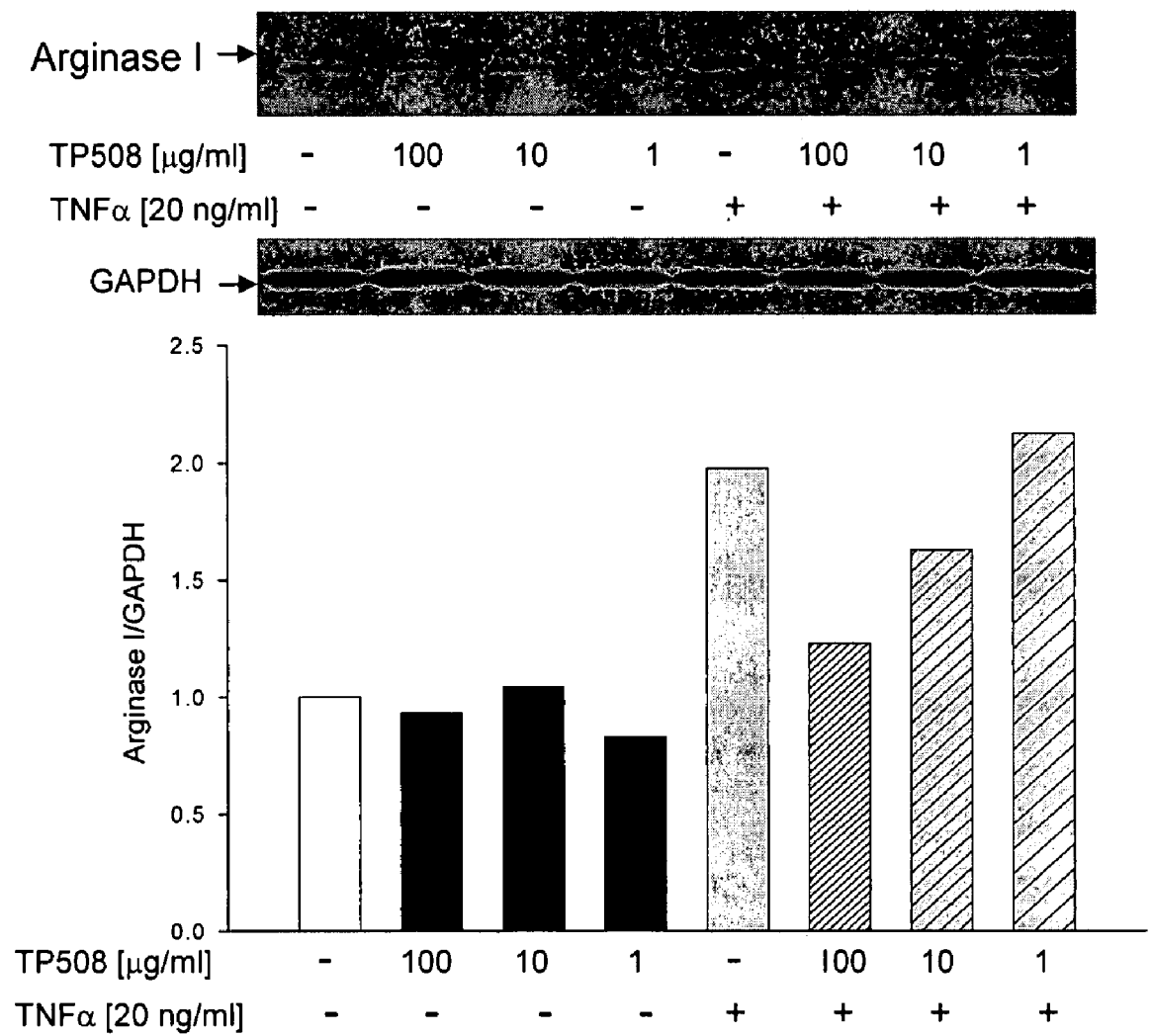
FIG. 2 shows X-ray films from western blot experiments and a corresponding bar graph of ratios of densitometry readings from the bands on the western blot showing a dose-response effect of TP508 on arginase 1 upregulation by TNFα. HCAE cells were pretreated with TP508 at the indicated concentration for 1 h before stimulation with TNFα for 24 h and cell lysates were analyzed for arginase 1 expression by immunoblotting. Densitometric analysis shows relative intensities of arginase 1 expression.

Western blots of HCAE cell lysates, using antibody specific for human type-1 arginase showed that TNFα treatment caused a significant increase in the expression of arginase 1 (ARG1) relative to control cultures (FIG. 1). As shown in FIGS. 1 and 2, TP508 treatment alone had no effect on ARG1 expression, but completely blocked the TNFα-induced increase in ARG1 expression. The TP508 inhibition of TNFα stimulated ARG1 expression is dose dependent with half maximal inhibition occurring at a TP508 concentration of 10 µg/ml (FIG. 2). Therefore, TP508 appears to block TNFα-induced signals that lead to an increase in ARG1. This inhibitory effect of TP508 appears to be specific for a subset of TNFα effects, since TNFα stimulated phosphorylation of Erk1/2 and p70 S6 kinase were not inhibited by TP508.

Example 3

TP508 Stimulates eNOS Expression and eNOS Phosphorylation

Figure 3:
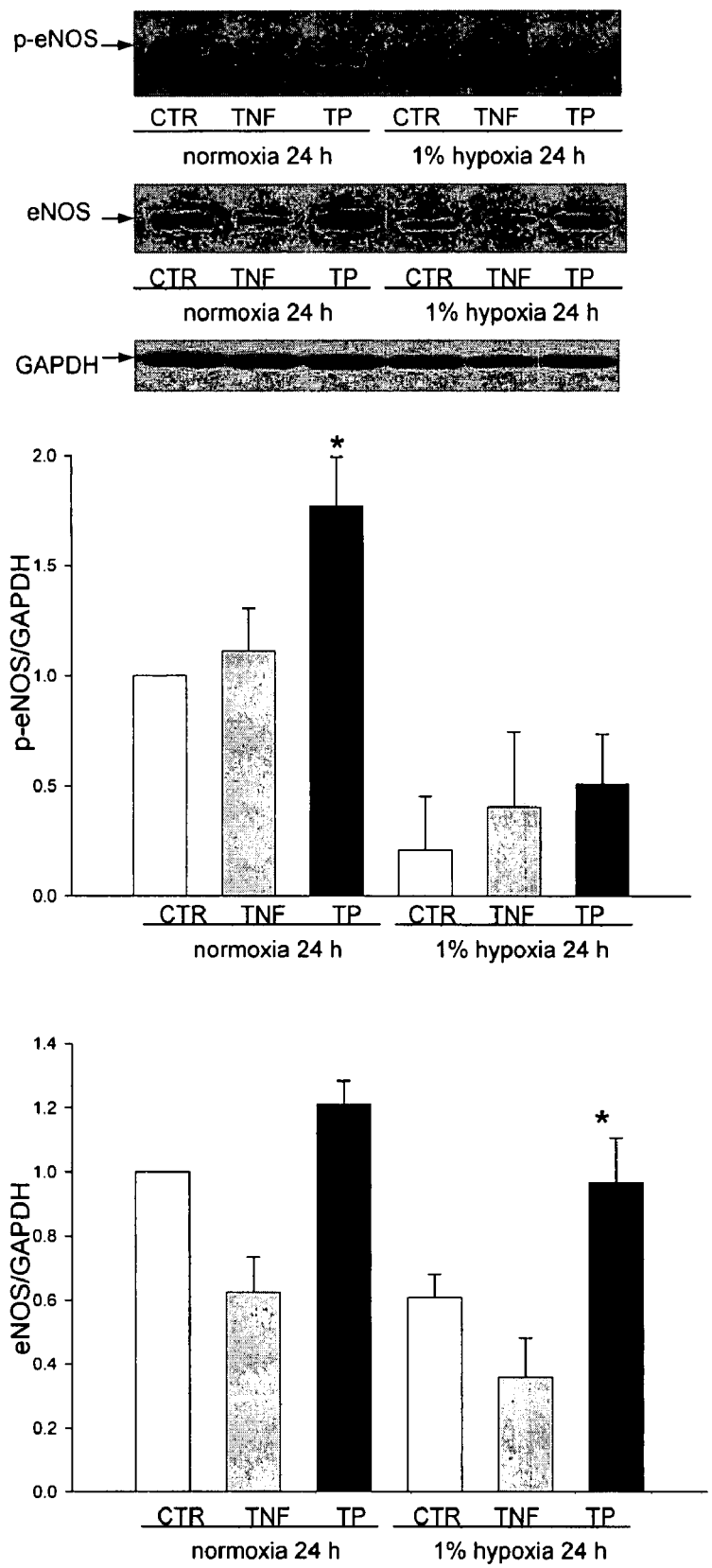
FIG. 3 shows X-ray films from western blots and corresponding bar graphs of ratios of densitometry readings from the bands on the western blots from experiments showing the effect of TP508 on expression and phosphorylation (activation) of eNOS. HCAE cells were stimulated with TP508 or TNFα and incubated in normoxic or 1% oxygen (hypoxic) conditions for 24 h. Cell lysates were analyzed for eNOS activation by immunoblotting using antibody specific for eNOS phosphorylated at S1177. After stripping, the membrane was reprobed with antibodies for total eNOS and GAPDH. Corresponding densitometric data represent the mean±SD of 3 independent experiments [* signifies $p<0.05$; CTR vs. TP(*) (normoxia); CTR vs. TP(*) (hypoxia)].
Figure 4:
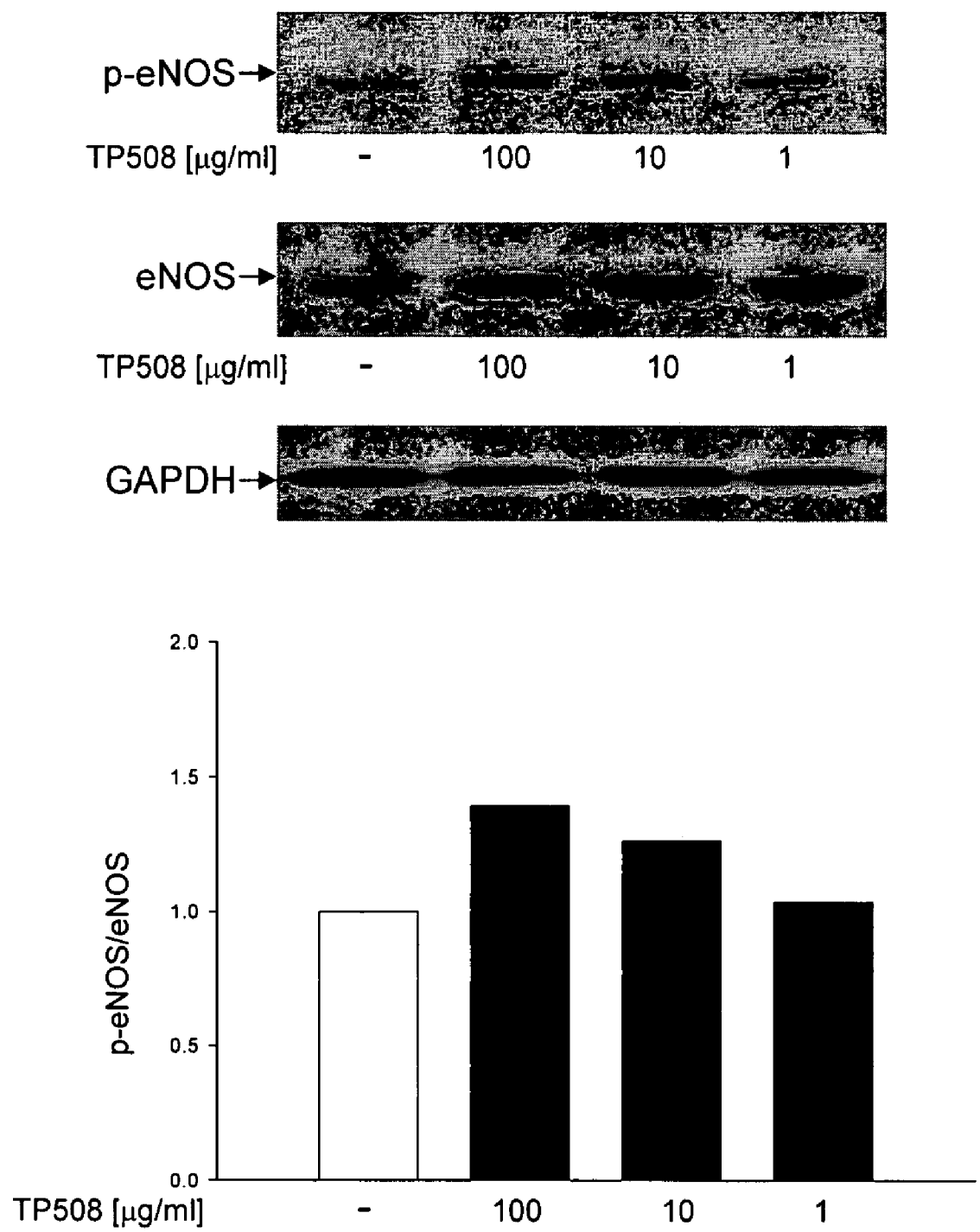
FIG. 4 shows X-ray films from western blot experiments and corresponding bar graphs of ratios of densitometry readings from the bands on the western blots from experiments examining the dose dependence of the effects of TP508 on eNOS activation. HCAE cells were treated with TP508 at the indicated concentrations for 24 h and analyzed for eNOS activity and expression as in FIG. 3. Densitometric analysis shows changes in eNOS phosphorylation relative to total eNOS after TP508 treatment.

Western blots of HCAE cell lysates, using antibody specific for eNOS phosphorylated at S1177 showed that TNFα treatment, or exposure of cells to hypoxic conditions (1% $O_2$) for 24 h, reduced the expression of eNOS by 65% and 45%, respectively, relative to normoxic controls (FIG. 3). As shown, TP508 prevented the decreased expression of eNOS caused by hypoxia to retain eNOS expression levels at levels similar to those seen in cells cultured under normoxic conditions. In contrast, TP508 addition together with TNFα was not able to inhibit the TNFα induced decrease in eNOS expression (not shown). Under normoxic and hypoxic conditions, TP508 increased eNOS phosphorylation relative to normoxic and hypoxic control cultures 1.8-fold and 2.5-fold, respectively (FIG. 3). Although some of this phosphorylation may be due to increased expression of eNOS, the increased phosphorylation cannot be explained by increased expression alone. Additional experiments examining the effect of TP508 on eNOS expression and phosphorylation in cells cultured under normoxic conditions confirmed that TP508 stimulated eNOS phosphorylation and showed that this effect is dose dependent with half maximal response at ~10 µg/ml (FIG. 4).

Example 4

TP508 Upregulates eNOS mRNA

Figure 6:
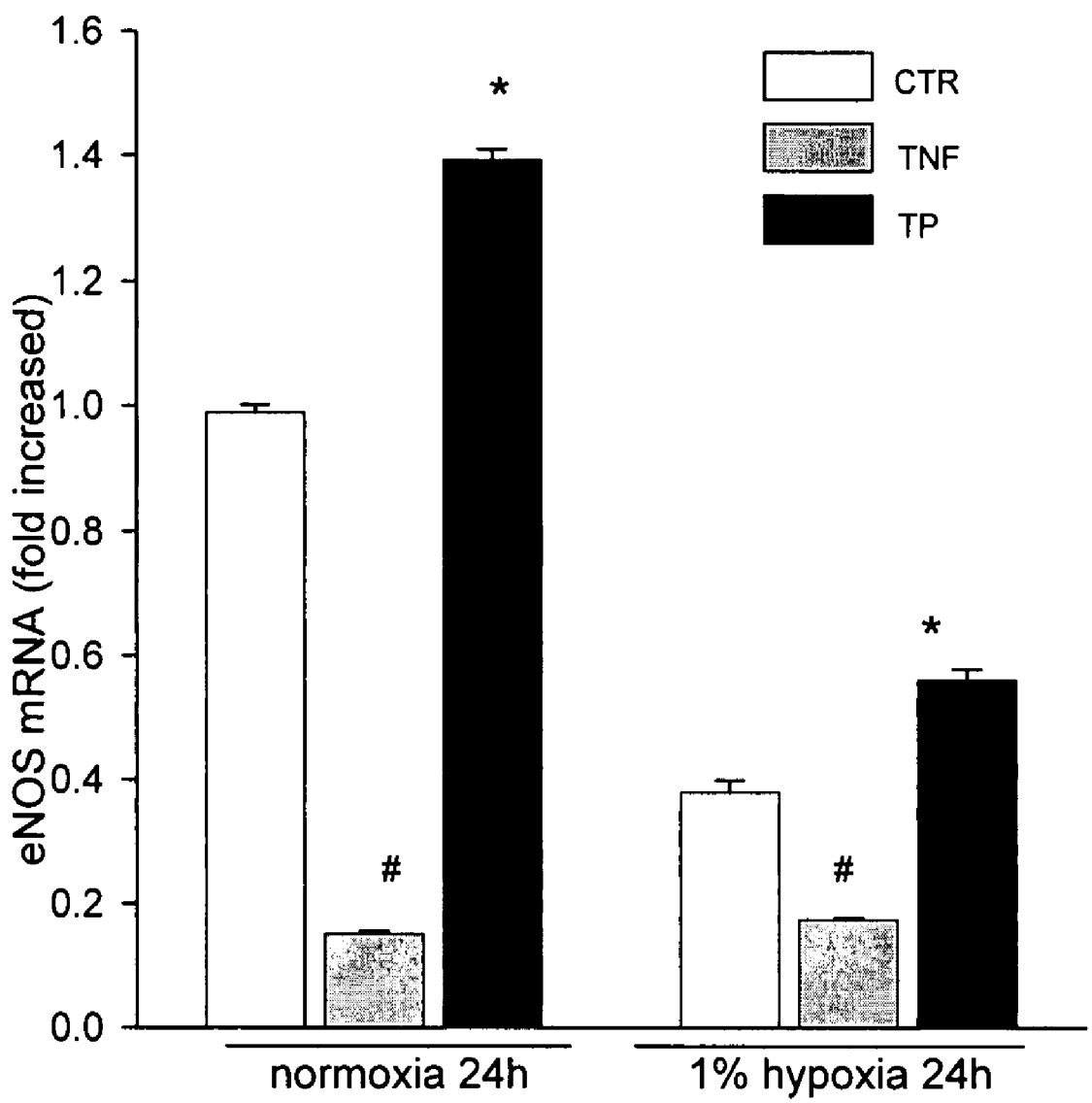
FIG. 6 is a bar graph of data from quantitative analysis of eNOS mRNA expression. HCAE cells were stimulated with TP508 or TNFα, and incubated in normoxic or hypoxic (1% oxygen) conditions for 24 h. RNA was analyzed for eNOS expression using SYBR Green real-time PCR. $p<0.05$ when compared with absence of TP508 (CTR) for each condition.

Consistent with the protein expression data, RT-PCR analysis of mRNA from HCAE cells showed that TP508 upregulates eNOS mRNA expression (FIG. 5). This effect of TP508 is shown at 25 cycles of RT-PCR where an eNOS mRNA band is seen in TP508-treated cells, but not in control cells. In contrast, TNFα treatment drastically decreased expression relative to controls as demonstrated after 30 cycles of RT-PCR. To quantify this effect of TP508, we used SYBR Green real-time PCR analysis of reverse transcribed mRNA samples. As shown in FIG. 6, after 24 h of culture under normoxic conditions, TP508 increased the level of eNOS mRNA by 40% relative to controls (p<0.05). In contrast, TNFα decreased the eNOS mRNA level by ~80%. A 24-hour exposure of the cells to hypoxia (1% oxygen) also decreased the control levels of eNOS mRNA by ~60%. TP508 treatment of these cells partially prevented the hypoxia induced decrease. As shown, TP508 treated hypoxic cells had eNOS mRNA levels ~40% over those of hypoxic control cells (p<0.05).

Example 5

TP508 Potentiates the Ability of VEGF to Signal eNOS Phosphorylation

Human coronary artery endothelial (HCAE) cells (Lonza Walkersville, Inc., Walkersville, Md.) were cultured in the presence or absence of TP508 [50 µg/ml] in normoxic and hypoxic [1% $O_2$] conditions for 24 h and then stimulated with the angiogenic growth factor, human VEGF [50 ng/ml] for 1 or 5 min. Human VEGF-induced eNOS activation was determined by Western blotting using an antibody recognizing the activated form of eNOS (phosphorylated at S1177) (Cell Signaling, Danvers, Mass.). The membrane was re-probed with anti-GAPDH (glyceraldehyde-3-phosphate dehydrogenase) antibody to show equal protein loading. A bar graph representing densitometric analysis of the activated eNOS Western blot after different treatments is shown in FIG. 8.

Figure 8:
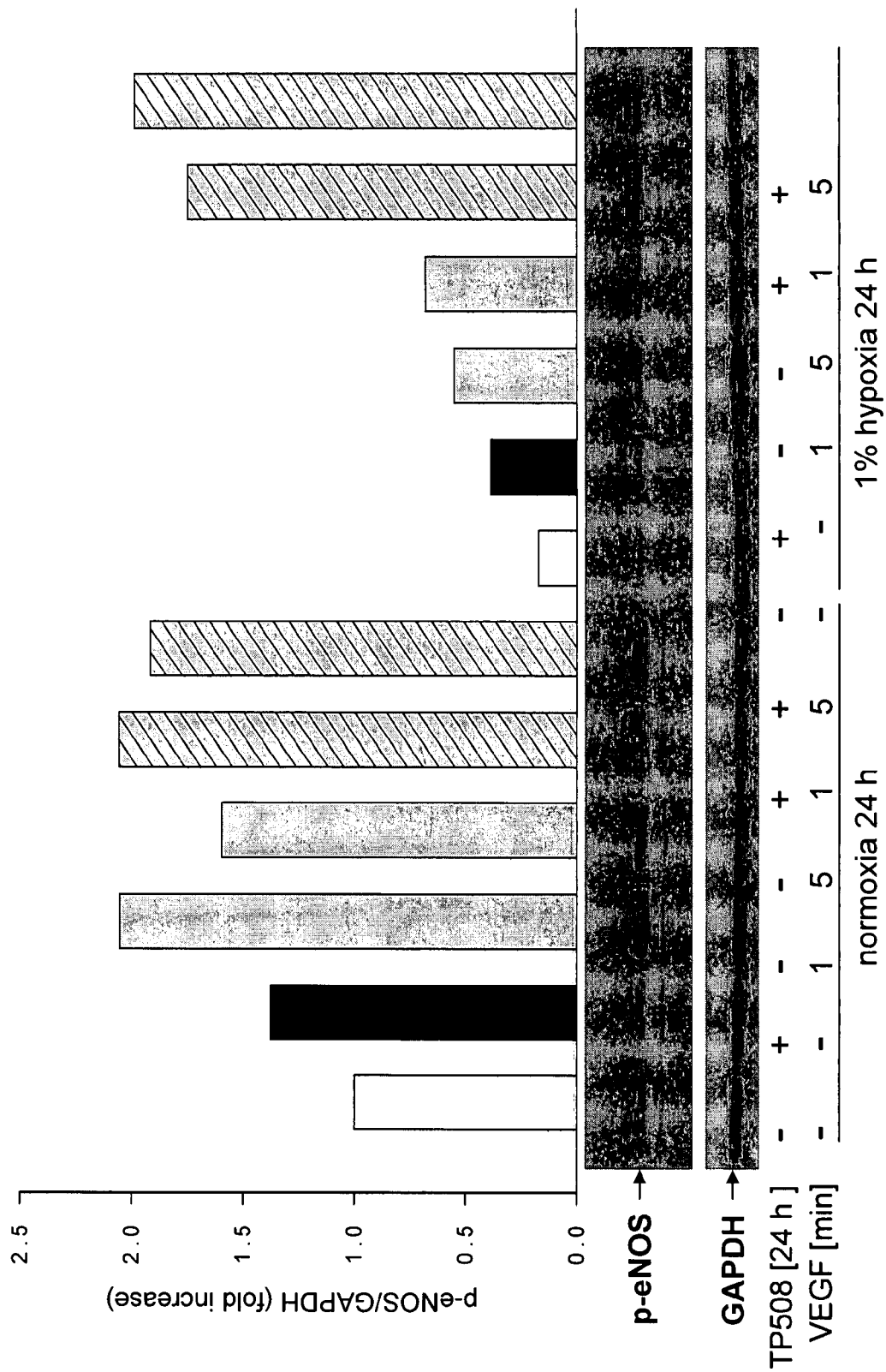
FIG. 8 is a graph showing densitometric analysis of a Western blot of activated endothelial nitric oxide synthase (eNOS) in HCAE cells following treatments with TP508, VEGF or a combination thereof.

As shown in FIG. 8, in normoxic cells, human VEGF induces transient phosphorylation of eNOS on serine 1177 to activate the enzyme which is maximum at 1 minute (2-fold) and has declined after 5 minutes stimulation. If cells were pretreated with TP508 prior to human VEGF stimulation, the phosphorylation of eNOS was prolonged and remained near maximum stimulation for 5 minutes. Thus, TP508 potentiates the ability of human VEGF to signal eNOS phosphorylation by extending the period of maximal stimulation.

In hypoxic cells (cultured in 1% $O_2$ for 24 hours), the level of human VEGF-stimulated eNOS phosphorylation is decreased ~4 fold at 1 min treatment compared to normoxic cells. Thus, hypoxia significantly reduces human VEGF-stimulated activation of eNOS. However, hypoxic cells pretreated with TP508 showed human VEGF-induced activation of eNOS at levels equivalent to that seen in normoxic cells. Thus, TP508 treatment of hypoxic cells restores the ability of human VEGF to stimulate eNOS activation to the level observed in normoxic cells.

Example 6

TP508 Enhances Endothelial Cell Migration towards VEGF

The ability of a test substance to attract endothelial cells and stimulate their migration through pores in the membrane is one of several tests to determine the angiogenic potential of test substances. FIG. 9A shows the design of experiments to measure migration of endothelial cells toward a chemoattractant. Prior to migration assay, cells were cultured with or without TP508 to determine the effect of TP508 on endothelial migration.

Human coronary artery endothelial (HCAE) cells (Lonza Walkersville, Inc., Walkersville, Md.) were cultured in the absence (control) or presence of TP508 [50 µg/ml] ("TP pret" in FIG. 9A and FIG. 9B) for 24 hours. Transmembrane cell migration assays were performed using BD FluoroBlok inserts (BD Bioscience, Bedford, Mass.) as described by the vendor. Control or TP508 pretreated cells were added into the top of the inserts. Human VEGF [10 ng/ml] (V) or medium alone (C) was added to the lower chamber of the insert plate as a chemoattractant. Endothelial migration was performed in normoxic or 1% hypoxic conditions. After a 22-hour incubation, cells were labeled post-migration with Calcein AM and measured by detecting the fluorescence of the cells that migrated to the underside of the insert membrane.

FIG. 9B shows the effect of TP508 treatment on migration of endothelial cells toward the angiogenic factor human VEGF (human recombinant VEGF-A 165, R&D System, Minneapolis, Minn.).

The results show that human VEGF stimulates normal control endothelial cell migration by ~2 fold relative to media control cells when assayed in normoxic conditions (180%) and slightly less (~150%) under hypoxic conditions relative to media control cells. Endothelial cells that were pretreated with TP508 showed cell migration toward human VEGF ~5-fold and ~4 fold relative to media controls when cells were assayed under normoxic and hypoxic conditions, respectively. TP508 pretreatment, thus, enhances endothelial migration toward human VEGF 2- to 3-fold relative to untreated control cells. Since this cell migration assay is one measure of the angiogenic potential of cells, these results demonstrate that TP508 treatment more than doubles the angiogenic potential of human VEGF for endothelial cells under normoxic conditions as well as under hypoxic conditions where angiogenic responses to human VEGF are diminished.

Example 7

TP508 Increases Angiogenic Response of Endothelial Cells toward Human VEGF

Invasion of endothelial cells through a Matrigel matrix is one of many assays used to determine the angiogenic potential of test substances and is thought to be more predictive of angiogenesis in vivo than a simple chemotactic assay through open membrane pores since the cells must degrade and invade the matrix to move into and through the pores in the membrane. FIG. 10A shows the design of experiments to measure invasion of endothelial cells through Matrigel toward a chemoattractant.

Human coronary artery endothelial (HCAE) cells (Lonza Walkersville, Inc., Walkersville, Md.) were cultured in the absence (control) or presence of TP508 [50 µg/ml] (TP pret) for 24 hours. Endothelial cell invasion assays were performed using BD BioCoat™ Angiogenesis System (BD Bioscience, Bedford, Mass.) which utilizes FluoroBlok inserts coated with BD Matrigel Matrix (BD Bioscience, Bedford, Mass.). Control or TP508 pretreated cells were added into the top of the inserts. Medium containing human VEGF [10 ng/ml human recombinant VEGF-A 165aa, R&D System, Minneapolis, Minn.] (V) or medium alone (C) was added to the lower chamber of the insert plate as a chemoattractant to determine angiogenic response to human VEGF. Endothelial cell invasion was performed in normoxic or hypoxic (1% $O_2$) conditions. After 22 hours of incubation, cells were labeled post-invasion with Calcein AM and measured by detecting the fluorescence of the cells that migrated to the underside of insert membrane.

FIG. 10B shows the effect of TP508 treatment on invasion of endothelial cells toward human VEGF. The results show that control endothelial cells assayed in normoxic conditions or under hypoxic conditions are not stimulated by human VEGF to degrade Matrigel and migrate through the membrane toward human VEGF. In contrast, endothelial cells that were pre-incubated with TP508 show increased invasive properties over control cells that were not pretreated with TP508. In addition, these cells now respond to human VEGF (~50% more invasion than observed in TP508 pretreated cells without human VEGF and nearly twice as much invasion as control cells toward VEGF). These results demonstrate the ability of TP508 treatment to increase the ability of endothelial cells to respond angiogenically to human VEGF under conditions where non-TP508 treated control cells do not respond at all to human VEGF treatment.

Example 8

Effects of TP508 on VEGF mRNA Expression in Normoxic and Hypoxic HCMVE Cells

Figure 11:
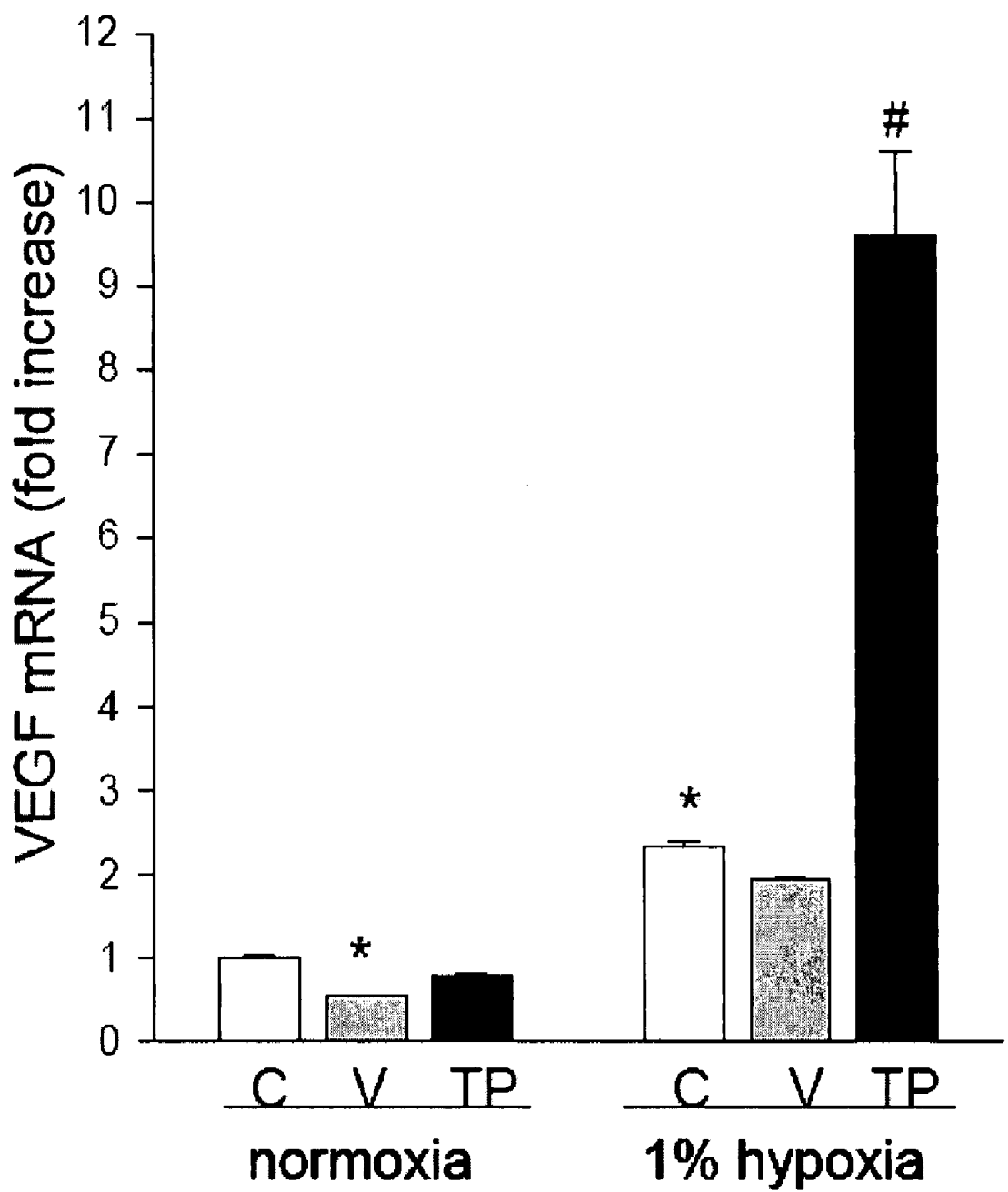
FIG. 11 is a graph showing the increase in VEGF mRNA in human cardiac microvascular endothelial cells treated with VEGF or with TP508 under normal oxygen conditions or hypoxic conditions.

Human cardiac microvascular endothelial (HCMVE) cells were treated with VEGF (10 ng/ml) (V) or TP508 (50 µg/ml) (TP) and cultured in normoxic or 1% hypoxic conditions for 24 h. Real-time PCR analyses show changes in steady-state levels of VEGF mRNA after treatment. Data from one experiment performed in triplicate are shown in FIG. 11 as mean±SD. *$p<0.01$ compared to control (C) cells in normoxia. #$p<0.01$ compared to control (C) cells in hypoxia.

Real-time PCR analyses showed that VEGF stimulation decreased VEGF mRNA expression (2-fold) compared to control cell in normoxic condition. As expected, hypoxia increased VEGF mRNA (2.4-fold) compared to normoxic control cells. TP508 treatment had no effect on steady-state level of VEGF mRNA in normoxic cells. However, hypoxic cells treated with TP508 expressed ~4-fold and ~10-fold higher levels of VEGF mRNA expression compared to control hypoxic or control normoxic cells, respectively (FIG. 11). In contrast, VEGF stimulation had no effect, or decreased VEGF mRNA in hypoxic cells. By this experiment, TP508 enhances the effect of hypoxia to up-regulate VEGF expression.

Example 9

Effect of TP508 Pre-Treatment on Carbachol Induced Relaxation

Rat aortic rings (endothelial cell layer intact) were prepared. Rings were treated with no TP508 (control) or 1 mM TP508 for 1 hour. Rings were contracted with 500 nM norepinephrine, followed by increasing doses of carbachol (0, 1, 10, 100, 500, 750, 1000 and 5000 nM). Mean values±SEM are shown; n=2 animals.

Norepinephrine contracted rings, with intact endothelium, relax in response to increasing doses of carbachol (Furchgott, R. F. and Zawadzki, J. V., Nature 288. 373-376 (1980)). If TP508 is a smooth muscle relaxant, TP508 treatment prior to a norepinephrine-carbachol dosing regimen should result in an increase in carbachol induced relaxation compared to the control, i.e., a shift of the carbachol dose response curve to the left relative to the control curve.

Figure 12:
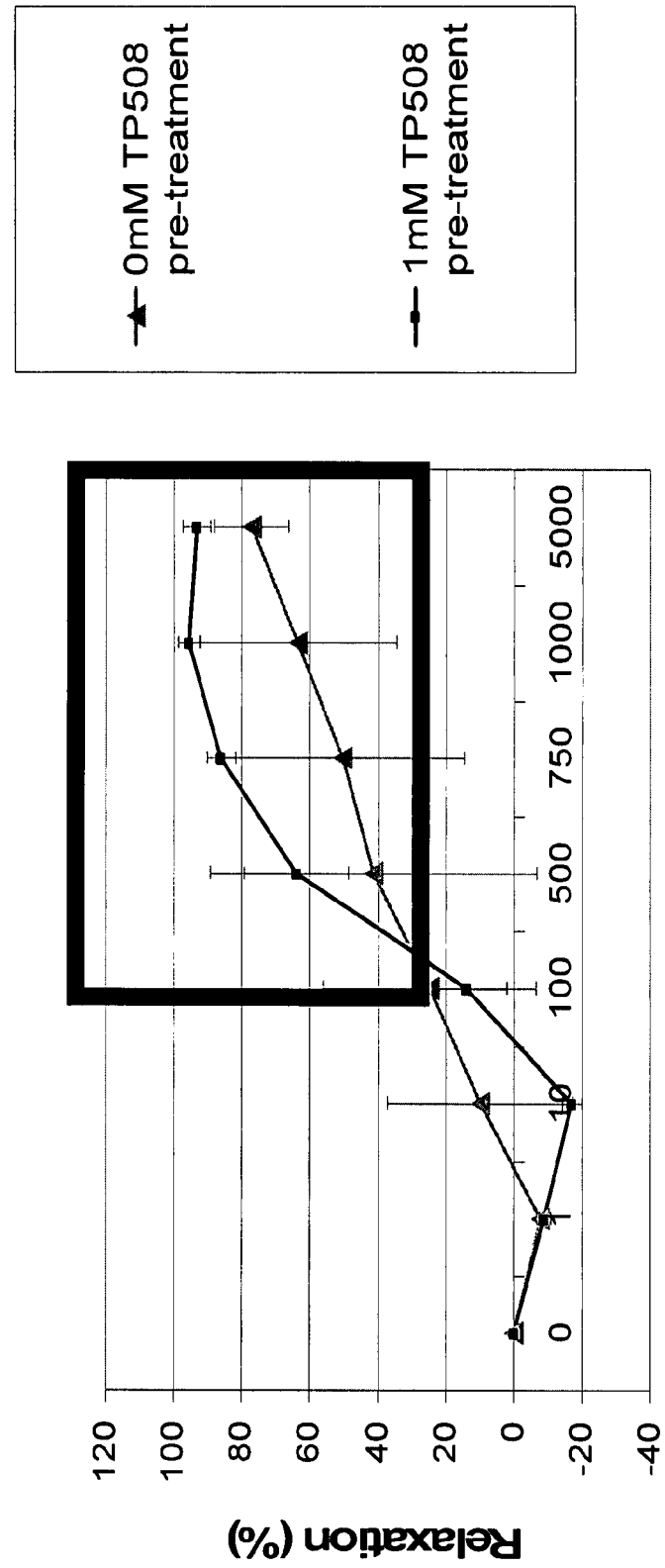
FIG. 12 is a graph of data from measurements on rings of rat aorta to assess the relaxant effect of TP508.

FIG. 12 demonstrates that at increased carbachol concentrations (greater than 250 nM; rectangular box) TP508 pretreated rings showed increased relaxation relative to controls. Furthermore, TP508 pre-treatment leads to a sigmoidal carbachol dose response curve. The control rings produced a linear carbachol dose response curve.

Example 10

Studies on Human Endothelial Cells

HMVEC (Human Microvascular Endothelial Cells)

Experiments using microarrays showed TP508 to prevent the increase in arginase 1 (ARG1) and decrease in endothelial nitric oxide synthase (eNOS) expression expected response to hypoxia. Studies on HMVECs are relevant to peripheral vascular disease, and renal vascular disease, for example.

HAE (Human Aortic Endothelial Cells)

HAE cells were used to study downstream regulatory elements. After 30 minutes of incubation under normoxic conditions, TP508 decreased phosphorylation of intracellular signal-regulating kinase 1 and 2 (ERK 1/2) and the serine/threonine kinase p70S6, and increased phosphorylation of focal adhesion kinase (FAK).

HAE cells were treated with tumor necrosis factor alpha (TNFα), increasing expression of ARG1. Pretreatment with TP508 inhibited the TNFα-induced increase in ARG1 only. This suggests that TP508 can reverse cytokine effects on the nitric oxide (NO) pathway. Under normoxic conditions, TP508 increased phosphorylated eNOS (p-eNOS) and eNOS in cells with and without TNFα/hypoxic treatment.

Studies on HAE cells are relevant to hypertension, atherosclerosis, aortic stenosis, and aortic aneurysm, for example.

TABLE 5

HAE SUMMARY

| Treatment | Responses | | |
|---|---|---|---|
| Cells treated with TP508 (normoxic) | ERK 1/2 activation decreased | p70S6 activation decreased | FAK activation increased |
| Cells pretreated with TP508, then TNFα | Inhibited the TNFα-induced increase in ARG1 | No effect on ERK1/2 phosphorylation | No effect on p70S6 phosphorylation |
| TP508 treatment with and without TNFα | Increased eNOS expression | Increased eNOS activation | |

HLME (Human Lung Microvascular Endothelial Cells; Alternatively, HLMVE Cells)

HLME cells were tested with VEGF, TP508 and serum-deprivation. Both lines observed showed increased survival when treated with both VEGF and TP508. VEGF alone increased survival at lower levels, and TP508 alone had little effect.

VEGF, eNOS, VEGFR1 and VEGFR2 were observed responding to TP508 treatment under hypoxic and normoxic conditions. When HLME cells were studied under normoxic conditions, only eNOS was positively regulated by TP508 treatment. When HLME cells were studied under hypoxic conditions, all four of these genes were upregulated at the mRNA level over the hypoxic untreated control.

TABLE 6

HLME SUMMARY

| Treatment | Responses | |
|---|---|---|
| Cells were deprived of serum, treated with VEGF and TP508 | Treating with TP508 alone did not increase cell survival rate | Treating with VEGF and TP508 increased survival beyond VEGF alone. |
| Cells treated with TP508: normoxic | eNOS expression was up regulated | VEGF, VEGFR1 and VEGFR2 expression: no effect |
| Cell treated with TP508: hypoxic | eNOS expression was up regulated | VEGF, VEGFR1 and VEGFR2 expression were upregulated |

Studies on HLME cells are relevant to asthma, acute lung injury, pulmonary artery hypertension, cystic fibrosis, and inflammatory lung disease, for example.

Example 11

Effects on Endothelial Function/Dysfunction in Isolated Coronary Arterioles

Coronary microvessels (arterioles) were isolated at day 60 from hearts of adult Yucatan swine that had undergone chronic occlusion of the left circumflex coronary artery (LCX) using an ameroid constrictor, and from nonischemic left anterior descending arteries (LAD) as described. Subepicardial arteriolar branches (60-100 μm internal diameter and 1 to 1.5 mm in length without branches, in situ) were carefully dissected from the LAD or LCX. Each arteriole was cannulated with glass micropipettes and pressurized to 60 cm $H_2O$ intraluminal pressure without flow. Internal diameters of the vessel were measured throughout the experiment using video microscopic techniques incorporated with MacLab (ADInstruments, Inc) data acquisition system. Following the development of tone (spontaneous constriction to about 70% of maximal diameter), we determined the concentration to diameter relationship for endothelium-dependent NO-mediated vasodilators adenosine (0.1 nM to 10 μM) and serotonin (0.1 nM to 1 μM), ATP sensitive potassium channel opener pinacidil (0.1 μM to 3 μM), and endothelium-independent vasodilator sodium nitroprusside (1 nM to 0.1 mM). The vasodilatory responses to these agonists were established before and after extraluminal incubation of arterioles. At the end of the experiments, each vessel was relaxed with 100 μM sodium nitroprusside in a physiologically balanced calcium-free salt solution containing ethylenediaminetetraacetic acid (EDTA, 1 mM) to obtain its maximal diameter at 60 cm $H_2O$ intraluminal pressure. All diameter changes in response to agonists were normalized to this dilation and expressed as a percentage of maximal dilation.

To determine if chronic ischemia in this model of LCX occlusion created coronary artery endothelial dysfunction and if TP508 treatment affected NO signaling, coronary arterioles were isolated from nonischemic branches of left anterior descending arteries (LAD) and from occluded, ischemic, LCX of TP508- and placebo-treated hearts. The isolated arterioles were then treated ex vivo with adenosine, serotonin, sodium nitroprusside, or pinacidil. If arterioles have endothelial dysfunction with impaired NO production, they should show diminished vasodilation in response to adenosine and serotonin (which are endothelium-dependent NO-mediated vasodilators), but not to sodium nitroprusside and pinacidil, which relax smooth muscle cells independent of endothelial cell response by donating NO to activate cyclic GMP and opening smooth muscle cell ATP-sensitive potassium channels, respectively.

Figure 13A:
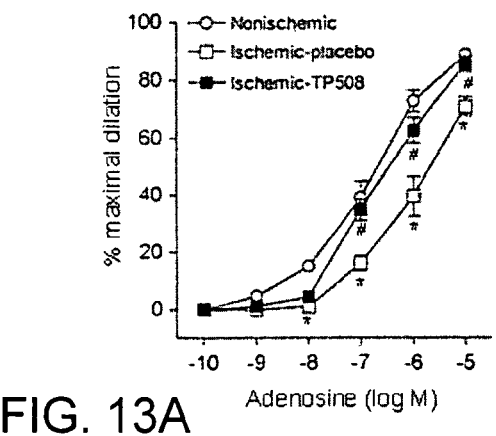
FIGS. 13A-13D are graphs showing the extent of dilation of coronary arterioles from ischemic hearts under conditions as shown.
Figure 13B:
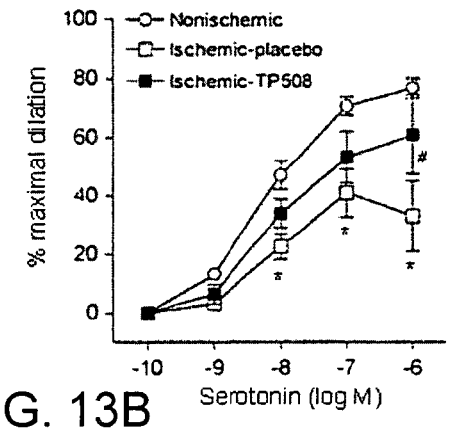
Figure 13C:
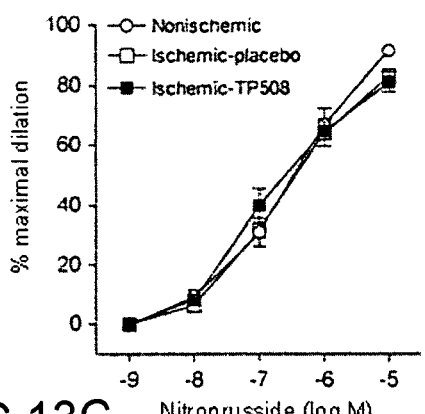
Figure 13D:
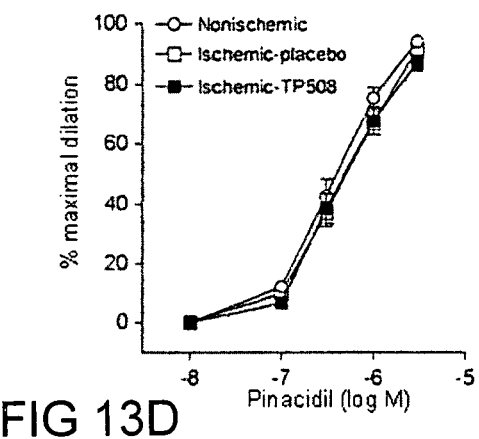

Ischemic arterioles show significantly diminished dilation responses to adenosine or serotonin relative to nonischemic vessels (FIGS. 13A and 13B). As shown, ischemia causes a rightward shift in the dose-response curve with ischemic arterioles requiring an order of magnitude more drug to achieve the same degree of dilation as nonischemic arterioles. This effect of hypoxia was not seen when isolated vessels were exposed to nitroprusside or pinacidil (FIGS. 13C and 13D). Thus, hypoxic arterioles dilate normally in response to NO delivered via NO donor and to a smooth muscle relaxing drug, but demonstrate classic endothelial dysfunction with diminished ability of endothelial cells to produce NO in response to serotonin and adenosine.

TP508 significantly increased arteriolar response to adenosine and serotonin relative to the responses of arterioles isolated from ischemic placebo-treated hearts (FIGS. 13A and 13B). Response to adenosine, in fact, appears to be restored in arterioles isolated from ischemic TP508-treated hearts to the level seen in nonischemic control arterioles (FIG. 13A).

Figure 13E:
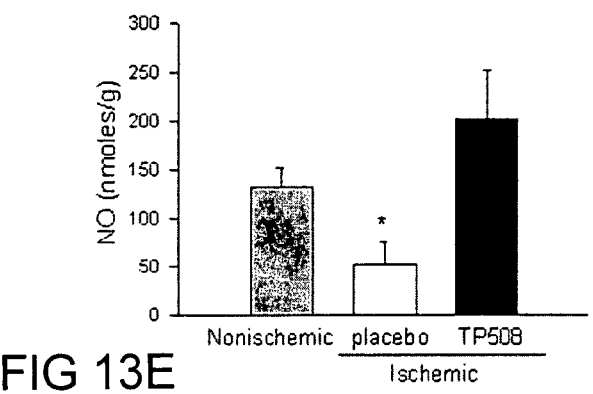
FIG. 13E is a bar graph showing results of treating arterioles isolated from nonischemic and ischemic hearts with either placebo or TP508, and analyzing for NO production.

To confirm that this TP508 effect on vasodilation represented a reversal of endothelial dysfunction in these arterioles, we determined the effect of hypoxia and TP508 on the ability of these arterioles to generate NO and the levels of eNOS expression. As shown in FIG. 13E, NO production by isolated arterioles from the ischemic LCX of placebo-treated hearts was decreased relative to nonischemic control arterioles from the LAD. Arterioles from ischemic LCX of TP508-treated hearts, however, had levels of NO production that exceeded the nonischemic control level. PCR analysis of mRNA from a limited number of these arterioles showed that eNOS mRNA expression was decreased in arterioles from the ischemic LCX relative to nonischemic control arterioles (FIG. 13F). Similar to its effect on NO production, TP508 treatment restored eNOS mRNA expression in ischemic arterioles to a level similar to or greater than that found in nonischemic arterioles. These results suggest that TP508 reverses endothelial dysfunction in these arterioles by a process that includes the upregulation of eNOS allowing more NO production.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating hypertension in a subject comprising administering to the subject a therapeutically effective amount of a 12 to 23 amino acid thrombin peptide derivative comprising a serine esterase conserved sequence and a thrombin binding domain having the sequence Arg-Gly-Asp-Ala (SEQ ID NO: 16).

2. The method of claim 1, wherein the thrombin peptide derivative comprises an N-terminus which is unsubstituted and a C-terminus which is unsubstituted or a C-terminal amide represented by —C(O)NH$_2$ and the thrombin peptide derivative comprises a polypeptide having the amino sequence of Arg-Gly-Asp-Ala-Cys-X$_1$-Gly-Asp-Ser-Gly-Gly-Pro-X$_2$-Val (SEQ ID NO:1), wherein X$_1$ is Glu or Gln and X$_2$ is Phe, Met, Leu, His or Val.

3. The method of claim 1, wherein the thrombin peptide derivative comprises the amino acid sequence of Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), or a fragment thereof, comprising amino acids 10-18 of SEQ ID NO: 2, wherein X$_1$ is Glu or Gln and X$_2$ is Phe, Met, Leu, His or Val and the thrombin peptide derivative comprises an N-terminus which is unsubstituted and a C-terminus which is unsubstituted or a C-terminal amide represented by —C(O)NH$_2$.

4. The method of claim 2, wherein the thrombin peptide derivative is the polypeptide H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:3).

5. A method of treating hypertension in a subject comprising administering to the subject a peptide dimer comprising two 12 to 23 amino acid thrombin peptide derivatives which, independently, comprise a serine esterase conserved sequence, and a thrombin binding domain having the sequence Arg-Gly-Asp-Ala (SEQ ID NO: 16); and wherein the dimer is essentially free of monomer.

6. The method of claim 5, wherein the thrombin peptide derivatives each comprise an N-terminus which is unsubstituted; and a C-terminus which is unsubstituted or a C-terminal amide represented by —C(O)NH$_2$.

7. The method of claim 5, wherein the thrombin peptide derivatives each comprise the amino acid sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), wherein X$_1$ is Glu or Gln and X$_2$ is Phe, Met, Leu, His or Val, or a fragment thereof, comprising amino acids 10-18 of SEQ ID NO:2, the thrombin peptide derivatives each comprise an N-terminus which is unsubstituted, and a C-terminus which is unsubstituted or a C-terminal amide represented by —C(O)NH$_2$ the dimer is essentially free of monomer; the thrombin peptide derivatives are the same, and the thrombin peptide derivatives are covalently linked through a disulfide bond.

8. The method of claim 5, wherein the thrombin peptide derivatives each comprise the amino acid sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), wherein X$_1$ is Glu or Gln and X$_2$ is Phe, Met, Leu, His or Val, the thrombin peptide derivatives each comprise an N-terminus which is unsubstituted; and a C-terminus which is unsubstituted or a C-terminal amide represented by —C(O)NH$_2$, the dimer is essentially free of monomer; the thrombin peptide derivatives are the same, and the thrombin peptide derivatives are covalently linked through a disulfide bond.

9. The method of claim 8, wherein X$_1$ is Glu and X$_2$ is Phe.

10. The method of claim 5, wherein the peptide dimer comprises two thrombin peptide derivatives, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6), wherein the thrombin peptide derivatives are covalently linked by a disulfide bond.

11. The method of claim 5, wherein the peptide dimer is represented by the following structural formula:

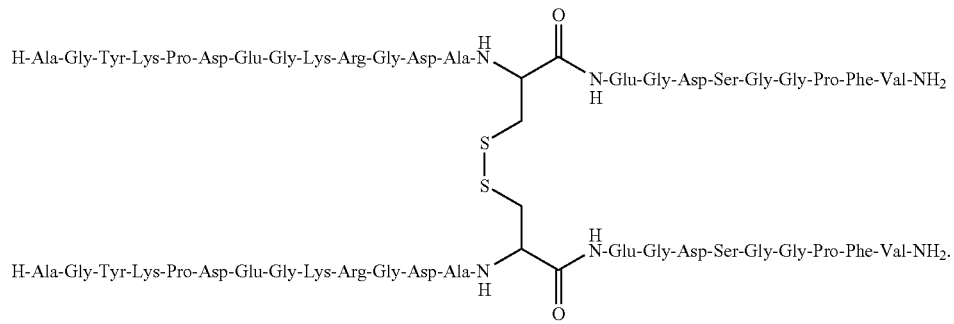

12. The method of claim 1 wherein the method further comprises administering to the subject a therapeutically effective amount of an angiogenic growth factor.

13. The method of claim 5, wherein the method further comprises administering to the subject a therapeutically effective amount of an angiogenic growth factor.

14. The method of claim 11, wherein the method further comprises administering to the subject a therapeutically effective amount of an angiogenic growth factor.

15. A method of treating radiation damage in a subject comprising administering to the subject a therapeutically effective amount of a 12 to 23 amino acid thrombin peptide derivative comprising a serine esterase conserved sequence and a thrombin binding domain having the sequence Arg-Gly-Asp-Ala (SEQ ID NO: 16).

16. The method of claim 15, wherein the thrombin peptide derivative comprises an N-terminus which is unsubstituted and a C-terminus which is unsubstituted or a C-terminal amide represented by —C(O)NH$_2$ and the thrombin peptide derivative comprises a polypeptide having the amino sequence of Arg-Gly-Asp-Ala-Cys-X$_1$-Gly-Asp-Ser-Gly-Gly-Pro-X$_2$-Val (SEQ ID NO:1), wherein X$_1$ is Glu or Gln and X$_2$ is Phe, Met, Leu, His or Val.

17. The method of claim 15, wherein the thrombin peptide derivative comprises the amino acid sequence of Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), or a fragment thereof, comprising amino acids 10-18 of SEQ ID NO: 2, wherein X$_1$ is Glu or Gln and X$_2$ is Phe, Met, Leu, His or Val and the thrombin peptide derivative comprises an N-terminus which is unsubstituted and a C-terminus which is unsubstituted or a C-terminal amide represented by —C(O)NH$_2$.

18. A method of treating radiation damage in a subject comprising administering to the subject a therapeutically effective amount of the polypeptide H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:3).

19. A method of treating radiation damage in a subject comprising administering to the subject a peptide dimer comprising two 12 to 23 amino acid thrombin peptide derivatives which, independently, comprise a serine esterase conserved sequence and a thrombin binding domain having the sequence Arg-Gly-Asp-Ala (SEQ ID NO: 16).

20. The method of claim 19, wherein the thrombin peptide derivatives each comprise an N-terminus which is unsubstituted; and a C-terminus which is unsubstituted or a C-terminal amide represented by —C(O)NH$_2$.

21. The method of claim 19, wherein the thrombin peptide derivatives each comprise the amino acid sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), wherein X$_1$ is Glu or Gln and X$_2$ is Phe, Met, Leu, His or Val, or a fragment thereof, comprising amino acids 10-18 of SEQ ID NO:2, the thrombin peptide derivatives each comprise an N-terminus which is unsubstituted, and a C-terminus which is unsubstituted or a C-terminal amide represented by —C(O)NH$_2$, the dimer is essentially free of monomer; the thrombin peptide derivatives are the same, and the thrombin peptide derivatives are covalently linked through a disulfide bond.

22. The method of claim 19, wherein the thrombin peptide derivatives each comprise the amino acid sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), wherein X$_1$ is Glu or Gln and X$_2$ is Phe, Met, Leu, His or Val, the thrombin peptide derivatives each comprise an N-terminus which is unsubstituted; and a C-terminus which is unsubstituted or a C-terminal amide represented by —C(O)NH$_2$, the dimer is essentially free of monomer; the thrombin peptide derivatives are the same, and the thrombin peptide derivatives are covalently linked through a disulfide bond.

23. The method of claim 22, wherein X$_1$ is Glu and X$_2$ is Phe.

24. The method of claim 19, wherein the peptide dimer comprises two thrombin peptide derivatives, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6), wherein the thrombin peptide derivatives are covalently linked by a disulfide bond.

25. A method of treating radiation damage in a subject comprising administering to the subject a peptide dimer represented by the following structural formula:

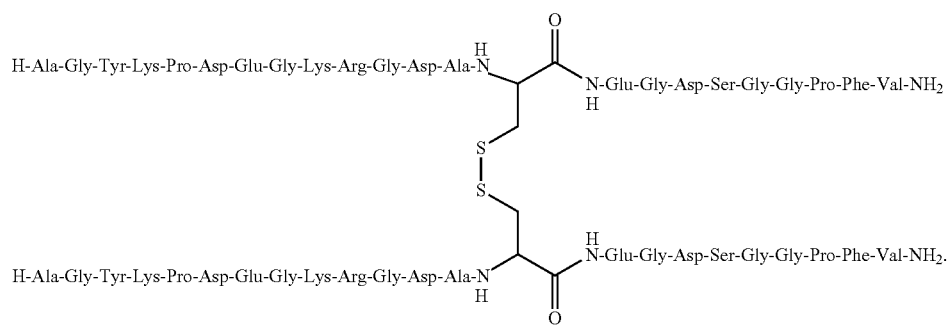

26. The method of claim 15, wherein the method further comprises administering to the subject a therapeutically effective amount of an angiogenic growth factor.

27. The method of claim 19, wherein the method further comprises administering to the subject a therapeutically effective amount of an angiogenic growth factor.

28. The method of claim 25, wherein the method further comprises administering to the subject a therapeutically effective amount of an angiogenic growth factor.

* * * * *

UNITED STATES PATENT AND TRADEMARK OFFICE
CERTIFICATE OF CORRECTION

PATENT NO. : 8,334,259 B2  Page 1 of 1
APPLICATION NO. : 12/311130
DATED : December 18, 2012
INVENTOR(S) : Darrell H. Carney et al.

It is certified that error appears in the above-identified patent and that said Letters Patent is hereby corrected as shown below:

In the Claims

Column 64, Line 17.
Claim 7.
Insert --,-- after "NH2".

Signed and Sealed this
Third Day of March, 2015

Michelle K. Lee
*Deputy Director of the United States Patent and Trademark Office*

SEQUENCE LISTING

<160> NUMBER OF SEQ ID NOS: 40

<210> SEQ ID NO 1
<211> LENGTH: 14
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 6
<223> OTHER INFORMATION: Xaa = Glu or Gln
<220> FEATURE:
<221> NAME/KEY: VARIANT
<222> LOCATION: 13
<223> OTHER INFORMATION: Xaa = Phe, Met, Leu, His or Val

<400> SEQUENCE: 1

Arg Gly Asp Ala Cys Xaa Gly Asp Ser Gly Gly Pro Xaa Val
 1               5                  10

<210> SEQ ID NO 2
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 15
<223> OTHER INFORMATION: Xaa = Glu or Gln
<220> FEATURE:
<221> NAME/KEY: VARIANT
<222> LOCATION: 22
<223> OTHER INFORMATION: Xaa = Phe, Met, Leu, His or Val
<220> FEATURE:
<223> OTHER INFORMATION: Ala at position 1 is optionally N-acylated
<220> FEATURE:
<223> OTHER INFORMATION: Val at position 23 is optionally C-amidated

<400> SEQUENCE: 2

Ala Gly Tyr Lys Pro Asp Glu Gly Lys Arg Gly Asp Ala Cys Xaa Gly
 1               5                  10                  15

Asp Ser Gly Gly Pro Xaa Val
            20

<210> SEQ ID NO 3
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Ala at position 1 is unmodified
<220> FEATURE:
<223> OTHER INFORMATION: Val at position 23 is amidated with -NH2

<400> SEQUENCE: 3

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 4
<211> LENGTH: 14
<212> TYPE: PRT
<213> ORGANISM: Artificial Sequence
<220> FEATURE:
<223> OTHER INFORMATION: thrombin peptide derivative

```
<220> FEATURE:
<221> NAME/KEY: VARIANT
<222> LOCATION: 5
<223> OTHER INFORMATION: Xaa = Ala, Gly, Ser or S-protected Cys
<220> FEATURE:
<221> NAME/KEY: VARIANT
<222> LOCATION: 6
<223> OTHER INFORMATION: Xaa = Glu or Gln
<220> FEATURE:
<221> NAME/KEY: VARIANT
<222> LOCATION: 13
<223> OTHER INFORMATION: Xaa = Phe, Met, Leu, His or Val

<400> SEQUENCE: 4

Arg Gly Asp Ala Xaa Xaa Gly Asp Ser Gly Gly Pro Xaa Val
 1               5                  10

<210> SEQ ID NO 5
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 14
<223> OTHER INFORMATION: Xaa = Ala, Gly, Ser or S-protected Cys
<220> FEATURE:
<221> NAME/KEY: VARIANT
<222> LOCATION: 15
<223> OTHER INFORMATION: Xaa = Glu or Gln
<220> FEATURE:
<221> NAME/KEY: VARIANT
<222> LOCATION: 22
<223> OTHER INFORMATION: Xaa = Phe, Met, Leu, His or Val

<400> SEQUENCE: 5

Ala Gly Tyr Lys Pro Asp Glu Gly Lys Arg Gly Asp Ala Xaa Xaa Gly
 1               5                  10                  15

Asp Ser Gly Gly Pro Xaa Val
            20

<210> SEQ ID NO 6
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Ala at position 1 is optionally N-acylated
<220> FEATURE:
<223> OTHER INFORMATION: Val at position 23 is optionally C-amidated

<400> SEQUENCE: 6

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 7
<211> LENGTH: 10
<212> TYPE: PRT
<213> ORGANISM: Artificial Sequence
<220> FEATURE:
<223> OTHER INFORMATION: thrombin peptide derivative

<400> SEQUENCE: 7

Glu Gly Lys Arg Gly Asp Ala Cys Glu Gly
 1               5                  10
```

```
<210> SEQ ID NO 8
<211> LENGTH: 22
<212> TYPE: PRT
<213> ORGANISM: Artificial Sequence
<220> FEATURE:
<223> OTHER INFORMATION: complementary peptide of domain of thrombin

<400> SEQUENCE: 8

Lys Gly Ser Pro Thr Val Thr Phe Thr Gly Ile Pro Cys Phe Pro Phe
1               5                   10                  15

Ile Arg Leu Val Thr Ser
            20

<210> SEQ ID NO 9
<211> LENGTH: 10
<212> TYPE: PRT
<213> ORGANISM: Artificial Sequence
<220> FEATURE:
<223> OTHER INFORMATION: complementary peptide of domain of thrombin

<400> SEQUENCE: 9

Thr Phe Thr Gly Ile Pro Ser Phe Pro Phe
1               5                   10

<210> SEQ ID NO 10
<211> LENGTH: 23
<212> TYPE: PRT
<213> ORGANISM: Artificial Sequence
<220> FEATURE:
<223> OTHER INFORMATION: complementary peptide of domain of thrombin

<400> SEQUENCE: 10

Arg Pro Met Phe Gly Leu Leu Pro Phe Ala Pro Leu Arg Thr Leu Pro
1               5                   10                  15

Leu Ser Pro Pro Gly Lys Gln
            20

<210> SEQ ID NO 11
<211> LENGTH: 10
<212> TYPE: PRT
<213> ORGANISM: Artificial Sequence
<220> FEATURE:
<223> OTHER INFORMATION: complementary peptide of domain of thrombin

<400> SEQUENCE: 11

Lys Pro Phe Ala Pro Leu Arg Thr Leu Pro
1               5                   10

<210> SEQ ID NO 12
<211> LENGTH: 622
<212> TYPE: PRT
<213> ORGANISM: Homo sapiens

<400> SEQUENCE: 12

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Gly Ala Leu Glu Ser Ser Thr Ala Thr
65                  70                  75                  80
```

```
Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510
```

```
Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 13
<211> LENGTH: 12
<212> TYPE: PRT
<213> ORGANISM: Artificial Sequence
<220> FEATURE:
<223> OTHER INFORMATION: serine esterase conserved sequence
<220> FEATURE:
<221> NAME/KEY: VARIANT
<222> LOCATION: 2
<223> OTHER INFORMATION: Xaa = Ala or Ser
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 11
<223> OTHER INFORMATION: Xaa = Phe, Met, Leu, His or Val

<400> SEQUENCE: 13

Asp Xaa Cys Xaa Gly Asp Ser Gly Gly Pro Xaa Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: serine esterase conserved sequence

<400> SEQUENCE: 14

Cys Glu Gly Asp Ser Gly Gly Pro Phe Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: serine esterase conserved sequence
<220> FEATURE:
<221> NAME/KEY: VARIANT
<222> LOCATION: 2
<223> OTHER INFORMATION: Xaa = Glu or Gln
<220> FEATURE:
<221> NAME/KEY: VARIANT
<222> LOCATION: 9
<223> OTHER INFORMATION: Xaa = Phe, Met, Leu, His or Val

<400> SEQUENCE: 15

Cys Xaa Gly Asp Ser Gly Gly Pro Xaa Val
1               5                   10
```

```
<210> SEQ ID NO 16
<211> LENGTH: 4
<212> TYPE: PRT
<213> ORGANISM: Artificial Sequence
<220> FEATURE:
<223> OTHER INFORMATION: thrombin peptide

<400> SEQUENCE: 16

Arg Gly Asp Ala
 1

<210> SEQ ID NO 17
<211> LENGTH: 14
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Arg at position 1 is optionally N-acylated
<220> FEATURE:
<223> OTHER INFORMATION: Val at position 14 is optionally C-amidated

<400> SEQUENCE: 17

Arg Gly Asp Ala Cys Glu Gly Asp Ser Gly Gly Pro Phe Val
 1               5                  10

<210> SEQ ID NO 18
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Asp at position 1 is optionally N-acylated
<220> FEATURE:
<223> OTHER INFORMATION: Phe at position 33 is optionally C-amidated

<400> SEQUENCE: 18

Asp Asn Met Phe Cys Ala Gly Tyr Lys Pro Asp Glu Gly Lys Arg Gly
 1               5                  10                  15

Asp Ala Cys Glu Gly Asp Ser Gly Gly Pro Phe Val Met Lys Ser Pro
            20                  25                  30

Phe

<210> SEQ ID NO 19
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 20
<223> OTHER INFORMATION: Xaa = Glu or Gln
<220> FEATURE:
<221> NAME/KEY: VARIANT
<222> LOCATION: 27
<223> OTHER INFORMATION: Xaa = Phe, Met, Leu, His or Val
<220> FEATURE:
<223> OTHER INFORMATION: Asp at position 1 is optionally N-acylated
<220> FEATURE:
<223> OTHER INFORMATION: Phe at position 33 is optionally C-amidated
```

```
<400> SEQUENCE: 19

Asp Asn Met Phe Cys Ala Gly Tyr Lys Pro Asp Glu Gly Lys Arg Gly
 1               5                  10                  15

Asp Ala Cys Xaa Gly Asp Ser Gly Gly Pro Xaa Val Met Lys Ser Pro
            20                  25                  30

Phe

<210> SEQ ID NO 20
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 14
<223> OTHER INFORMATION: Xaa = Ala, Gly, Ser or S-protected Cys

<400> SEQUENCE: 20

Ala Gly Tyr Lys Pro Asp Glu Gly Lys Arg Gly Asp Ala Xaa Glu Gly
 1               5                  10                  15

Asp Ser Gly Gly Pro Phe Val
            20

<210> SEQ ID NO 21
<211> LENGTH: 23
<212> TYPE: PRT
<213> ORGANISM: Artificial Sequence
<220> FEATURE:
<223> OTHER INFORMATION: thrombin peptide derivative

<400> SEQUENCE: 21

Ala Gly Tyr Lys Pro Asp Glu Gly Lys Arg Gly Asp Ala Ala Glu Gly
 1               5                  10                  15

Asp Ser Gly Gly Pro Phe Val
            20

<210> SEQ ID NO 22
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Ala at position 1 is unmodified
<220> FEATURE:
<223> OTHER INFORMATION: Val at position 23 is amidated with -NH2

<400> SEQUENCE: 22

Ala Gly Tyr Lys Pro Asp Glu Gly Lys Arg Gly Asp Ala Ala Glu Gly
 1               5                  10                  15

Asp Ser Gly Gly Pro Phe Val
            20

<210> SEQ ID NO 23
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 5, 19
<223> OTHER INFORMATION: Xaa = Ala, Gly, Ser or S-protected Cys
```

```
<400> SEQUENCE: 23

Asp Asn Met Phe Xaa Ala Gly Tyr Lys Pro Asp Glu Gly Lys Arg Gly
1               5                   10                  15

Asp Ala Xaa Glu Gly Asp Ser Gly Gly Pro Phe Val Met Lys Ser Pro
            20                  25                  30

Phe

<210> SEQ ID NO 24
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 5, 19
<223> OTHER INFORMATION: Xaa = Ala, Gly, Ser or S-protected Cys
<220> FEATURE:
<221> NAME/KEY: VARIANT
<222> LOCATION: 20
<223> OTHER INFORMATION: Xaa = Glu or Gln
<220> FEATURE:
<221> NAME/KEY: VARIANT
<222> LOCATION: 27
<223> OTHER INFORMATION: Xaa = Phe, Met, Leu, His or Val

<400> SEQUENCE: 24

Asp Asn Met Phe Xaa Ala Gly Tyr Lys Pro Asp Glu Gly Lys Arg Gly
1               5                   10                  15

Asp Ala Xaa Xaa Gly Asp Ser Gly Gly Pro Xaa Val Met Lys Ser Pro
            20                  25                  30

Phe

<210> SEQ ID NO 25
<211> LENGTH: 33
<212> TYPE: PRT
<213> ORGANISM: Artificial Sequence
<220> FEATURE:
<223> OTHER INFORMATION: thrombin peptide derivative

<400> SEQUENCE: 25

Asp Asn Met Phe Ala Ala Gly Tyr Lys Pro Asp Glu Gly Lys Arg Gly
1               5                   10                  15

Asp Ala Ala Glu Gly Asp Ser Gly Gly Pro Phe Val Met Lys Ser Pro
            20                  25                  30

Phe

<210> SEQ ID NO 26
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Asp at position 1 is unmodified
<220> FEATURE:
<223> OTHER INFORMATION: Phe at position 33 is amidated with -NH2

<400> SEQUENCE: 26

Asp Asn Met Phe Ala Ala Gly Tyr Lys Pro Asp Glu Gly Lys Arg Gly
1               5                   10                  15

Asp Ala Ala Glu Gly Asp Ser Gly Gly Pro Phe Val Met Lys Ser Pro
            20                  25                  30

Phe
```

```
<210> SEQ ID NO 27
<211> LENGTH: 33
<212> TYPE: PRT
<213> ORGANISM: Artificial Sequence
<220> FEATURE:
<223> OTHER INFORMATION: thrombin peptide derivative

<400> SEQUENCE: 27

Ala Gly Tyr Lys Pro Asp Glu Gly Lys Arg Gly Asp Ala Cys Glu Gly
 1               5                  10                  15

Asp Ser Gly Gly Pro Phe Val Met Lys Ser Pro Phe Asn Asn Arg Trp
            20                  25                  30

Tyr

<210> SEQ ID NO 28
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 15
<223> OTHER INFORMATION: Xaa = Glu or Gln
<220> FEATURE:
<221> NAME/KEY: VARIANT
<222> LOCATION: 22
<223> OTHER INFORMATION: Xaa = Phe, Met, Leu, His or Val

<400> SEQUENCE: 28

Ala Gly Tyr Lys Pro Asp Glu Gly Lys Arg Gly Asp Ala Cys Xaa Gly
 1               5                  10                  15

Asp Ser Gly Gly Pro Xaa Val Met Lys Ser Pro Phe Asn Asn Arg Trp
            20                  25                  30

Tyr

<210> SEQ ID NO 29
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Ala at position 1 is unmodified
<220> FEATURE:
<223> OTHER INFORMATION: Tyr at position 33 is amidated with -NH2

<400> SEQUENCE: 29

Ala Gly Tyr Lys Pro Asp Glu Gly Lys Arg Gly Asp Ala Cys Glu Gly
 1               5                  10                  15

Asp Ser Gly Gly Pro Phe Val Met Lys Ser Pro Phe Asn Asn Arg Trp
            20                  25                  30

Tyr

<210> SEQ ID NO 30
<211> LENGTH: 22
<212> TYPE: PRT
<213> ORGANISM: Artificial Sequence
<220> FEATURE:
<223> OTHER INFORMATION: complementary peptide of domain of thrombin

<400> SEQUENCE: 30

Lys Gly Ser Pro Thr Val Thr Phe Thr Gly Ile Pro Cys Phe Pro Phe
 1               5                  10                  15

Ile Arg Leu Val Thr Ser
            20
```

```
<210> SEQ ID NO 31
<211> LENGTH: 22
<212> TYPE: PRT
<213> ORGANISM: Artificial Sequence
<220> FEATURE:
<223> OTHER INFORMATION: complementary peptide of domain of thrombin

<400> SEQUENCE: 31

Lys Gly Ser Pro Thr Val Thr Phe Thr Gly Ile Pro Ser Phe Pro Phe
 1               5                  10                  15

Ile Arg Leu Val Thr Ser
            20

<210> SEQ ID NO 32
<211> LENGTH: 10
<212> TYPE: PRT
<213> ORGANISM: Artificial Sequence
<220> FEATURE:
<223> OTHER INFORMATION: complementary peptide of domain of thrombin

<400> SEQUENCE: 32

Thr Phe Thr Gly Ile Pro Ser Phe Pro Phe
 1               5                  10

<210> SEQ ID NO 33
<211> LENGTH: 23
<212> TYPE: PRT
<213> ORGANISM: Artificial Sequence
<220> FEATURE:
<223> OTHER INFORMATION: complementary peptide of domain of thrombin

<400> SEQUENCE: 33

Arg Pro Met Phe Gly Leu Leu Pro Phe Ala Pro Leu Arg Thr Leu Pro
 1               5                  10                  15

Leu Ser Pro Pro Gly Lys Gln
            20

<210> SEQ ID NO 34
<211> LENGTH: 10
<212> TYPE: PRT
<213> ORGANISM: Artificial Sequence
<220> FEATURE:
<223> OTHER INFORMATION: complementary peptide of domain of thrombin

<400> SEQUENCE: 34

Leu Pro Phe Ala Pro Leu Arg Thr Leu Pro
 1               5                  10

<210> SEQ ID NO 35
<211> LENGTH: 24
<212> TYPE: DNA
<213> ORGANISM: Artificial Sequence
<220> FEATURE:
<223> OTHER INFORMATION: PCR primer

<400> SEQUENCE: 35
gcaccggcat caccaggaag aaga                                          24

<210> SEQ ID NO 36
<211> LENGTH: 22
<212> TYPE: DNA
<213> ORGANISM: Artificial Sequence
<220> FEATURE:
<223> OTHER INFORMATION: PCR primer
```

```
<400> SEQUENCE: 36
ccgccgccaa gaggacacca gt                                              22

<210> SEQ ID NO 37
<211> LENGTH: 19
<212> TYPE: DNA
<213> ORGANISM: Artificial Sequence
<220> FEATURE:
<223> OTHER INFORMATION: PCR primer

<400> SEQUENCE: 37
gcggctgcat gacattgag                                                  19

<210> SEQ ID NO 38
<211> LENGTH: 22
<212> TYPE: DNA
<213> ORGANISM: Artificial Sequence
<220> FEATURE:
<223> OTHER INFORMATION: PCR primer

<400> SEQUENCE: 38
gtcgcggtag agatggtcaa gt                                              22

<210> SEQ ID NO 39
<211> LENGTH: 14
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 5
<223> OTHER INFORMATION: Xaa = Ala, Gly, Ser or S-protected Cys

<400> SEQUENCE: 39

Arg Gly Asp Ala Xaa Glu Gly Asp Ser Gly Gly Pro Phe Val
  1               5                  10

<210> SEQ ID NO 40
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<221> NAME/KEY: VARIANT
<222> LOCATION: 15
<223> OTHER INFORMATION: Xaa = Glu or Gln
<220> FEATURE:
<221> NAME/KEY: VARIANT
<222> LOCATION: 22
<223> OTHER INFORMATION: Xaa = Phe, Met, Leu, His or Val
<220> FEATURE:
<223> OTHER INFORMATION: Ala at position 1 is unmodified
<220> FEATURE:
<223> OTHER INFORMATION: Val at position 23 is amidated with -NH2

<400> SEQUENCE: 40

Ala Gly Tyr Lys Pro Asp Glu Gly Lys Arg Gly Asp Ala Cys Xaa Gly
  1               5                  10                  15

Asp Ser Gly Gly Pro Xaa Val
              20
```